(12) United States Patent
Bruzzi et al.

(10) Patent No.: US 11,278,307 B2
(45) Date of Patent: Mar. 22, 2022

(54) THROMBECTOMY DEVICES WITH ASPIRATION

(71) Applicant: Vetex Medical Limited, Galway (IE)

(72) Inventors: Mark Bruzzi, Galway (IE); Saeid Kasiri Ghahi, Galway (IE); Paul Heneghan, Galway (IE)

(73) Assignee: Vetex Medical Limited, Galway (IE)

( * ) Notice: Subject to any disclaimer, the term of this patent is extended or adjusted under 35 U.S.C. 154(b) by 0 days.

(21) Appl. No.: 17/246,120

(22) Filed: Apr. 30, 2021

(65) Prior Publication Data

US 2021/0307779 A1    Oct. 7, 2021

Related U.S. Application Data

(63) Continuation of application No. 17/133,111, filed on Dec. 23, 2020, which is a continuation of application (Continued)

(30) Foreign Application Priority Data

Mar. 15, 2013    (EP) .................................... 13159640

(51) Int. Cl.
*A61B 17/3207* (2006.01)
*A61B 17/221* (2006.01)
(Continued)

(52) U.S. Cl.
CPC .... *A61B 17/320725* (2013.01); *A61B 17/221* (2013.01); *A61B 17/32056* (2013.01);
(Continued)

(58) Field of Classification Search
CPC .......... A61B 17/221; A61B 17/370725; A61B 17/00685; A61B 17/320016;
(Continued)

(56) References Cited

U.S. PATENT DOCUMENTS

| 4,909,789 A | 3/1990 | Taguchi et al. |
|---|---|---|
| 5,092,839 A | 3/1992 | Kipperman |

(Continued)

FOREIGN PATENT DOCUMENTS

| EP | 0117519 A1 | 9/1984 |
|---|---|---|
| EP | 1 736 106 A1 | 12/2006 |

(Continued)

OTHER PUBLICATIONS

U.S. Appl. No. 14/776,663 U.S. Pat. No. 10,813,663, filed Sep. 14, 2015, A Device Suitable for Removing Matter From Inside the Lumen and the Wall of a Body Lumen.

(Continued)

*Primary Examiner* — Tuan V Nguyen

(74) *Attorney, Agent, or Firm* — Schwegman Lundberg & Woessner, P.A.

(57) ABSTRACT

A thrombectomy device includes a handle at a proximal end portion of the device, a cage at a distal end portion of the device, the cage being moveable between an expanded orientation and a contracted orientation, and a first tube extending from the proximal end portion of the device to at least a proximal end portion of the cage. The device also includes a second tube extending from the proximal end portion of the device to at least a distal end portion of the cage, and a self-adjusting control assembly including a biasing element coupled to one of the first tube or the second tube. The biasing element exerts an axial force to urge the cage toward the expanded orientation.

13 Claims, 26 Drawing Sheets

Related U.S. Application Data

No. 15/936,635, filed on Mar. 27, 2018, now Pat. No. 10,874,421, which is a continuation of application No. 15/008,057, filed on Jan. 27, 2016, now Pat. No. 10,779,852, which is a continuation of application No. 14/776,633, filed as application No. PCT/IE2014/000005 on Mar. 18, 2014, now Pat. No. 10,813,663.

(51) Int. Cl.
*A61B 17/3205* (2006.01)
*A61B 17/00* (2006.01)
*A61B 17/32* (2006.01)

(52) U.S. Cl.
CPC ........... *A61B 17/320758* (2013.01); *A61B 17/320783* (2013.01); *A61B 2017/00685* (2013.01); *A61B 2017/2212* (2013.01); *A61B 2017/320008* (2013.01); *A61B 2017/320064* (2013.01); *A61B 2017/320733* (2013.01); *A61B 2217/005* (2013.01)

(58) Field of Classification Search
CPC ......... A61B 17/32002; A61B 17/3207; A61B 17/320708; A61B 17/32075; A61B 17/320758; A61B 17/320775; A61B 17/320783; A61B 2017/22079; A61B 2017/320008; A61B 2017/320024; A61B 2017/320028; A61B 2017/320032; A61B 2017/32004; A61B 2017/320069; A61B 2017/320716; A61B 2017/320733; A61B 2017/320741; A61B 2017/320772
See application file for complete search history.

(56) References Cited

U.S. PATENT DOCUMENTS

| | | |
|---|---|---|
| 5,135,517 A * | 8/1992 | McCoy .......... A61B 17/320783 604/531 |
| 5,156,610 A * | 10/1992 | Reger .............. A61B 17/32075 30/348 |
| 5,190,557 A | 3/1993 | Borodulin et al. |
| 5,370,653 A | 12/1994 | Cragg |
| 5,490,859 A * | 2/1996 | Mische .......... A61B 17/320725 606/159 |
| 5,573,530 A | 11/1996 | Fleury et al. |
| 5,720,764 A | 2/1998 | Naderlinger |
| 5,722,401 A | 3/1998 | Pietroski et al. |
| 5,772,674 A | 6/1998 | Nakhjavan |
| 5,795,322 A | 8/1998 | Boudewijn |
| 5,817,104 A | 10/1998 | Bilitz et al. |
| 5,836,868 A | 11/1998 | Ressemann et al. |
| 5,873,882 A * | 2/1999 | Straub ............ A61B 17/320783 606/159 |
| 5,972,019 A * | 10/1999 | Engelson ............. A61B 17/221 606/200 |
| 6,027,520 A | 2/2000 | Tsugita et al. |
| 6,066,158 A | 5/2000 | Engelson et al. |
| 6,129,739 A | 10/2000 | Khosravi |
| 6,146,396 A | 11/2000 | Konya et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,842 B1 | 3/2001 | Tu et al. |
| 6,371,970 B1 | 4/2002 | Khosravi et al. |
| 6,383,205 B1 | 5/2002 | Samson et al. |
| 6,454,775 B1 | 9/2002 | Demarais et al. |
| 6,530,939 B1 | 3/2003 | Hopkins et al. |
| 6,544,279 B1 | 4/2003 | Hopkins et al. |
| 6,558,405 B1 | 5/2003 | McInnes |
| 6,610,077 B1 | 8/2003 | Hancock et al. |
| 6,616,679 B1 | 9/2003 | Khosravi et al. |
| 6,620,182 B1 | 9/2003 | Khosravi et al. |
| 6,652,548 B2 | 11/2003 | Evans et al. |
| 6,656,203 B2 | 12/2003 | Roth et al. |
| 6,660,014 B2 | 12/2003 | Demarais et al. |
| 6,695,858 B1 | 2/2004 | Dubrul et al. |
| 6,702,830 B1 | 3/2004 | Demarais et al. |
| 6,945,977 B2 | 9/2005 | Demarais et al. |
| 7,014,647 B2 | 3/2006 | Brady et al. |
| 7,037,316 B2 | 5/2006 | McGuckin, Jr. |
| 7,083,633 B2 | 8/2006 | Morrill et al. |
| 7,220,269 B1 | 5/2007 | Ansel et al. |
| 7,507,246 B2 | 3/2009 | McGuckin et al. |
| 7,621,870 B2 | 11/2009 | Berrada et al. |
| 7,645,261 B2 | 1/2010 | Hinchliffe |
| 7,645,290 B2 | 1/2010 | Lucas |
| 7,655,016 B2 | 2/2010 | Demarais et al. |
| 7,749,220 B2 | 7/2010 | Schmaltz |
| 7,909,801 B2 | 3/2011 | Hinchliffe |
| 7,922,741 B2 | 4/2011 | Gilson et al. |
| 7,955,344 B2 | 6/2011 | Finitsis |
| 7,955,345 B2 | 6/2011 | Kucharczyk et al. |
| 7,981,128 B2 | 7/2011 | To et al. |
| 7,988,705 B2 | 8/2011 | Galdonik et al. |
| 7,993,363 B2 | 8/2011 | Demond et al. |
| 8,038,674 B2 | 10/2011 | Schmaltz |
| 8,043,313 B2 | 10/2011 | Krolik |
| 8,043,326 B2 | 10/2011 | Hancock et al. |
| 8,057,496 B2 | 11/2011 | Fischer, Jr. |
| 8,057,497 B1 | 11/2011 | Raju |
| 8,062,258 B2 | 11/2011 | Demarais et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,092,486 B2 | 1/2012 | Berrada et al. |
| 8,197,493 B2 | 6/2012 | Ferrera et al. |
| 8,221,489 B2 | 7/2012 | Issenmann et al. |
| 8,252,010 B1 | 8/2012 | Raju |
| 8,303,538 B2 | 11/2012 | Bonnette et al. |
| RE43,882 E | 12/2012 | Hopkins et al. |
| 8,343,167 B2 | 1/2013 | Henson |
| 8,361,095 B2 | 1/2013 | Osborne |
| 8,366,737 B2 | 2/2013 | Hancock et al. |
| 8,403,976 B2 | 3/2013 | Sachar et al. |
| 8,414,543 B2 | 4/2013 | McGuckin, Jr. et al. |
| 8,430,837 B2 | 4/2013 | Jenson et al. |
| 8,435,218 B2 | 5/2013 | Hinchliffe |
| 8,449,566 B2 | 5/2013 | Finitsis |
| 8,475,487 B2 | 7/2013 | Bonnette et al. |
| 8,480,697 B2 | 7/2013 | Kucharczyk et al. |
| 8,486,105 B2 | 7/2013 | Demond et al. |
| 8,512,352 B2 | 8/2013 | Martin |
| 8,545,514 B2 | 10/2013 | Ferrera |
| 8,562,639 B2 | 10/2013 | Khosravi et al. |
| 8,574,262 B2 | 11/2013 | Ferrera et al. |
| 8,585,713 B2 | 11/2013 | Ferrera et al. |
| 8,603,122 B2 | 12/2013 | Pokorney et al. |
| 8,617,201 B2 | 12/2013 | Hopkins et al. |
| 8,663,259 B2 | 3/2014 | Levine et al. |
| 8,668,713 B2 | 3/2014 | Horan et al. |
| 8,679,142 B2 | 3/2014 | Slee et al. |
| 8,758,424 B2 | 6/2014 | Sachar et al. |
| 8,764,779 B2 | 7/2014 | Levine et al. |
| 8,771,289 B2 | 7/2014 | Mohiuddin et al. |
| 8,784,442 B2 | 7/2014 | Jones et al. |
| 8,900,257 B2 | 12/2014 | Straub et al. |
| 8,926,680 B2 | 1/2015 | Ferrera et al. |
| 8,940,003 B2 | 1/2015 | Slee et al. |
| 8,945,143 B2 | 2/2015 | Ferrera et al. |
| 8,945,172 B2 | 2/2015 | Ferrera et al. |
| 8,956,384 B2 | 2/2015 | Berrada et al. |
| 9,017,294 B2 | 4/2015 | McGuckin, Jr. et al. |
| 9,050,127 B2 | 6/2015 | Bonnette et al. |
| 9,055,964 B2 | 6/2015 | Cartier et al. |
| 10,743,907 B2 | 8/2020 | Bruzzi et al. |
| 10,779,852 B2 | 9/2020 | Bruzzi et al. |
| 10,813,663 B2 | 10/2020 | Bruzzi et al. |
| 10,874,421 B2 | 12/2020 | Bruzzi et al. |
| 2001/0016751 A1 | 8/2001 | Trerotola |
| 2001/0031981 A1 | 10/2001 | Evans |

(56) References Cited

U.S. PATENT DOCUMENTS

| | | | |
|---|---|---|---|
| 2002/0010487 A1* | 1/2002 | Evans | A61B 17/221 606/180 |
| 2002/0026211 A1 | 2/2002 | Khosravi | |
| 2002/0188314 A1 | 12/2002 | Anderson et al. | |
| 2003/0055445 A1 | 3/2003 | Evans et al. | |
| 2003/0176884 A1 | 9/2003 | Berrada | |
| 2003/0220667 A1 | 11/2003 | Van Der Burg | |
| 2004/0039435 A1 | 2/2004 | Hancock | |
| 2004/0098033 A1 | 5/2004 | Leeflang et al. | |
| 2004/0219028 A1 | 11/2004 | Demarais et al. | |
| 2005/0027265 A1 | 2/2005 | Maki et al. | |
| 2006/0030878 A1 | 2/2006 | Anderson et al. | |
| 2006/0155305 A1 | 7/2006 | Freudenthal et al. | |
| 2006/0229645 A1 | 10/2006 | Bonnette et al. | |
| 2006/0253069 A1 | 11/2006 | Li et al. | |
| 2007/0156170 A1 | 7/2007 | Hancock | |
| 2007/0173883 A1 | 7/2007 | Keegan et al. | |
| 2007/0208367 A1 | 9/2007 | Fiorella et al. | |
| 2007/0250112 A1 | 10/2007 | Ravikumar | |
| 2008/0208211 A1 | 8/2008 | Uihlein | |
| 2009/0018565 A1 | 1/2009 | To et al. | |
| 2009/0099581 A1 | 4/2009 | Kim et al. | |
| 2009/0105722 A1 | 4/2009 | Fulkerson et al. | |
| 2009/0105737 A1 | 4/2009 | Fulkerson et al. | |
| 2009/0292307 A1 | 11/2009 | Razack | |
| 2010/0022951 A1 | 1/2010 | Ferrera et al. | |
| 2010/0036410 A1 | 2/2010 | Krolik et al. | |
| 2010/0094320 A1 | 4/2010 | Arat et al. | |
| 2010/0130850 A1 | 5/2010 | Pakter | |
| 2010/0174309 A1 | 7/2010 | Fulkerson et al. | |
| 2010/0185148 A1 | 7/2010 | Gillespie, III | |
| 2010/0185230 A1 | 7/2010 | Horan | |
| 2010/0217187 A1 | 8/2010 | Fulkerson et al. | |
| 2010/0249815 A1 | 9/2010 | Jantzen et al. | |
| 2010/0256600 A1 | 10/2010 | Ferrera | |
| 2010/0292724 A1 | 11/2010 | Ravikumar et al. | |
| 2010/0305678 A1 | 12/2010 | Alaswad | |
| 2010/0318097 A1 | 12/2010 | Ferrera et al. | |
| 2011/0082483 A1* | 4/2011 | Diamant | A61B 17/320725 606/159 |
| 2011/0087257 A1 | 4/2011 | To et al. | |
| 2011/0125181 A1 | 5/2011 | Brady et al. | |
| 2011/0160741 A1 | 6/2011 | Asano et al. | |
| 2011/0160757 A1 | 6/2011 | Ferrera et al. | |
| 2011/0160760 A1 | 6/2011 | Ferrera et al. | |
| 2011/0190797 A1 | 8/2011 | Fulkerson et al. | |
| 2011/0190806 A1 | 8/2011 | Wittens | |
| 2011/0238106 A1 | 9/2011 | Ferrera et al. | |
| 2011/0264132 A1 | 10/2011 | Strauss et al. | |
| 2011/0319917 A1 | 12/2011 | Ferrera et al. | |
| 2012/0016406 A1 | 1/2012 | Ferrera et al. | |
| 2012/0041460 A1 | 2/2012 | Ferrera et al. | |
| 2012/0041475 A1 | 2/2012 | Ferrera et al. | |
| 2012/0116440 A1 | 5/2012 | Leynov et al. | |
| 2012/0172662 A1 | 7/2012 | Kappel et al. | |
| 2012/0179181 A1 | 7/2012 | Straub et al. | |
| 2012/0238872 A1 | 9/2012 | Schwager | |
| 2012/0239064 A1* | 9/2012 | Cartier | A61B 17/320725 606/159 |
| 2012/0271231 A1 | 10/2012 | Agrawal | |
| 2012/0316600 A1 | 12/2012 | Ferrera et al. | |
| 2012/0330350 A1 | 12/2012 | Jones | |
| 2013/0066346 A1 | 3/2013 | Pigott | |
| 2013/0102996 A1 | 4/2013 | Strauss | |
| 2013/0289589 A1 | 10/2013 | Krolik et al. | |
| 2013/0289608 A1 | 10/2013 | Tanaka et al. | |
| 2013/0296916 A1 | 11/2013 | Monstadt | |
| 2014/0121672 A1 | 5/2014 | Folk | |
| 2014/0121758 A1 | 5/2014 | Ferrera et al. | |
| 2014/0128905 A1 | 5/2014 | Molaei | |
| 2014/0207177 A1 | 7/2014 | Horan et al. | |
| 2014/0214067 A1 | 7/2014 | Sachar et al. | |
| 2014/0228869 A1 | 8/2014 | Bonnette et al. | |
| 2014/0303658 A1 | 10/2014 | Bonnette et al. | |
| 2014/0336691 A1 | 11/2014 | Jones | |
| 2014/0343585 A1 | 11/2014 | Ferrera et al. | |
| 2014/0343595 A1 | 11/2014 | Monstadt | |
| 2014/0343596 A1 | 11/2014 | Slee et al. | |
| 2015/0005792 A1 | 1/2015 | Ahn | |
| 2015/0018928 A1 | 1/2015 | Sachar et al. | |
| 2015/0032138 A1 | 1/2015 | Jensen et al. | |
| 2015/0032144 A1 | 1/2015 | Holloway | |
| 2015/0112376 A1 | 4/2015 | Molaei et al. | |
| 2015/0133973 A1 | 5/2015 | Milner et al. | |
| 2015/0150672 A1 | 6/2015 | Ma | |
| 2015/0157346 A1 | 6/2015 | Ferrera et al. | |
| 2015/0182361 A1 | 7/2015 | Ferrera et al. | |
| 2015/0196380 A1 | 7/2015 | Berrada et al. | |
| 2015/0209058 A1 | 7/2015 | Ferrera et al. | |
| 2015/0216650 A1 | 8/2015 | Shaltis | |
| 2016/0038174 A1 | 2/2016 | Bruzzi et al. | |
| 2016/0206344 A1 | 7/2016 | Bruzzi et al. | |
| 2018/0271556 A1 | 9/2018 | Bruzzi et al. | |
| 2021/0228229 A1 | 7/2021 | Bruzzi et al. | |
| 2021/0251651 A1 | 8/2021 | Bruzzi et al. | |

FOREIGN PATENT DOCUMENTS

| | | |
|---|---|---|
| EP | 1310219 B1 | 3/2007 |
| EP | 2967614 A1 | 1/2016 |
| EP | 2967614 B1 | 11/2016 |
| EP | 3202340 A1 | 8/2017 |
| EP | 3305220 A1 | 4/2018 |
| EP | 3305221 A1 | 4/2018 |
| JP | S 63212339 A | 9/1988 |
| JP | H05137729 A | 6/1993 |
| JP | H 8509639 A | 10/1996 |
| JP | H10151136 A | 6/1998 |
| JP | 2000504263 A | 4/2000 |
| JP | 2003265488 A | 9/2003 |
| JP | 2003530903 A | 10/2003 |
| JP | 2004500171 A | 1/2004 |
| JP | 2004503265 A | 2/2004 |
| JP | 2006511266 A | 4/2006 |
| JP | 4330571 B2 | 11/2006 |
| JP | 2006305301 A | 11/2006 |
| JP | 2010532211 A | 10/2010 |
| JP | 2011526820 A | 10/2011 |
| JP | 2015506754 A | 3/2015 |
| JP | 2016513524 A | 5/2016 |
| JP | 6435280 B2 | 11/2018 |
| JP | 2019022755 A | 2/2019 |
| JP | 6763003 B2 | 9/2020 |
| JP | 2020195854 A | 12/2020 |
| JP | 2020195855 A | 12/2020 |
| WO | WO 91/04763 A1 | 4/1991 |
| WO | WO 97/17892 A1 | 5/1997 |
| WO | WO 98/50103 A1 | 11/1998 |
| WO | WO 01/08743 A1 | 2/2001 |
| WO | WO 01/19444 A1 | 3/2001 |
| WO | WO 01/39673 A1 | 6/2001 |
| WO | WO 01/74255 A1 | 10/2001 |
| WO | WO 01/87168 A1 | 11/2001 |
| WO | WO 01/28618 A3 | 12/2001 |
| WO | WO 02/11626 A3 | 8/2002 |
| WO | WO 02/11627 A3 | 11/2002 |
| WO | WO 03/018085 A2 | 3/2003 |
| WO | WO 02/094111 A3 | 4/2003 |
| WO | WO 02/094130 A3 | 10/2003 |
| WO | WO 03/077799 A3 | 4/2004 |
| WO | WO 05/046736 A2 | 5/2005 |
| WO | WO 05/055878 A2 | 6/2005 |
| WO | WO 05/112770 A1 | 12/2005 |
| WO | WO 06/107641 A2 | 10/2006 |
| WO | WO 06/110186 A2 | 10/2006 |
| WO | WO 07/061418 A2 | 5/2007 |
| WO | WO 08/097993 A2 | 8/2008 |
| WO | WO 09/021071 A2 | 2/2009 |
| WO | WO 09/067629 A2 | 5/2009 |
| WO | WO 09/079539 A1 | 6/2009 |
| WO | WO 09/086154 A2 | 7/2009 |
| WO | WO 09/089297 A2 | 7/2009 |
| WO | WO 09/105710 A1 | 8/2009 |
| WO | WO 09/114046 A2 | 9/2009 |

(56) References Cited

FOREIGN PATENT DOCUMENTS

| WO | WO 09/124288 A1 | 10/2009 |
|---|---|---|
| WO | WO 09/126935 A2 | 10/2009 |
| WO | WO 09/154441 A1 | 12/2009 |
| WO | WO 10/049121 A2 | 5/2010 |
| WO | WO 10/082187 A1 | 7/2010 |
| WO | WO 10/082188 A1 | 7/2010 |
| WO | WO 11/021119 A1 | 2/2011 |
| WO | WO 11/079111 A1 | 6/2011 |
| WO | WO-2011072149 A1 | 6/2011 |
| WO | WO 11/151910 A1 | 12/2011 |
| WO | WO 2011/151911 A1 | 12/2011 |
| WO | WO-2012009675 A2 | 1/2012 |
| WO | WO-2012065748 A1 | 5/2012 |
| WO | WO 12/156069 A1 | 11/2012 |
| WO | WO 13/109756 A2 | 7/2013 |
| WO | WO 14/004244 A1 | 1/2014 |
| WO | WO 14/055609 A1 | 4/2014 |
| WO | WO 14/070405 A1 | 5/2014 |
| WO | WO 14/074318 A1 | 5/2014 |
| WO | WO 14/085590 A1 | 6/2014 |
| WO | WO 14/127389 A2 | 8/2014 |
| WO | WO 14/127738 A1 | 8/2014 |
| WO | WO 14/141226 A1 | 9/2014 |
| WO | WO 14/150013 A1 | 9/2014 |
| WO | WO 14/154137 A1 | 10/2014 |
| WO | WO 15/057796 A1 | 4/2015 |

OTHER PUBLICATIONS

U.S. Appl. No. 15/936,635 U.S. Pat. No. 10,874,421, filed Mar. 27, 2018, Extraction Devices.
U.S. Appl. No. 17/133,111, filed Dec. 23, 2020, Thrombectomy Devices With Control Assemblies.
U.S. Appl. No. 15/008,057, filed Jan. 27, 2016, Device Suitable for Removing Matter From Inside the Lumen and the Wall of a Body Lumen.
U.S. Appl. No. 17/246,353, filed Apr. 30, 2021, Thrombectomy Devices With Maceration.
International Search Report and Written Opinion of International Application No. PCT/IE2014/000005, dated Jul. 7, 2014, (15 pages).
International Search Report and Written Opinion in pending International Application No. PCT/EP2015/075995 dated Apr. 21, 2016 (16 pages).
European Search Report for European Application No. 16201115.9, dated Jun. 14, 2017 (8 pages).
"U.S. Appl. No. 14/776,633, Advisory Action dated Jul. 11, 2018", 3 pgs.
"U.S. Appl. No. 14/776,633, Examiner Interview Summary dated Sep. 19, 2019", 3 pgs.
"U.S. Appl. No. 14/776,633, Final Office Action dated Mar. 27, 2018", 16 pgs.
"U.S. Appl. No. 14/776,633, Final Office Action dated Dec. 26, 2019", 17 pgs.
"U.S. Appl. No. 14/776,633, Non Final Office Action dated Jun. 11, 2019", 20 pgs.
"U.S. Appl. No. 14/776,633, Non Final Office Action dated Jun. 27, 2017", 13 pgs.
"U.S. Appl. No. 14/776,633, Notice of Allowance dated Jun. 25, 2020", 8 pgs.
"U.S. Appl. No. 14/776,633, Preliminary Amendment filed Apr. 13, 2017", 8 pgs.
"U.S. Appl. No. 14/776,633, Preliminary Amendment filed Sep. 14, 2015", 9 pgs.
"U.S. Appl. No. 14/776,633, Response filed Jun. 8, 2020 to Final Office Action dated Dec. 26, 2019", 12 pgs.
"U.S. Appl. No. 14/776,633, Response filed Jun. 27, 2018 to Final Office Action dated Mar. 27, 2018", 16 pgs.
"U.S. Appl. No. 14/776,633, Response filed Aug. 27, 2018 to Advisory Action dated Jul. 11, 2018", 16 pgs.

"U.S. Appl. No. 14/776,633, Response filed Sep. 20, 2019 to Non Final Office Action dated Jun. 11, 2019", 16 pgs.
"U.S. Appl. No. 14/776,633, Response filed Nov. 27, 2017 to Non Final Office Action dated Jun. 27, 2017", 16 pgs.
"U.S. Appl. No. 15/008,057 Examiner's Answer to Appeal Brief dated Aug. 2, 2018", 10 pages.
"U.S. Appl. No. 15/008,057, Appeal Brief filed Jun. 6, 2018", 27 pgs.
"U.S. Appl. No. 15/008,057, Appeal Decision mailed Apr. 23, 2020", 6 pgs.
"U.S. Appl. No. 15/008,057, Decision to Pre-Appeal Brief Conference Request mailed Mar. 21, 2018", 2 pgs.
"U.S. Appl. No. 15/008,057, Examiner Interview Summary dated Mar. 21, 2017", 3 pgs.
"U.S. Appl. No. 15/008,057, Examiner Interview Summary dated Jun. 3, 2016", 3 pgs.
"U.S. Appl. No. 15/008,057, Final Office Action dated Nov. 25, 2016", 20 pgs.
"U.S. Appl. No. 15/008,057, Non Final Office Action dated May 9, 2016", 20 pgs.
"U.S. Appl. No. 15/008,057, Non Final Office Action dated Dec. 15, 2017", 25 pgs.
"U.S. Appl. No. 15/008,057, Notice of Allowance dated May 11, 2020", 8 pgs.
"U.S. Appl. No. 15/008,057, Pre-Appeal Brief Conference Request filed Mar. 5, 2018", 7 pgs.
"U.S. Appl. No. 15/008,057, Preliminary Amendment filed Jan. 27, 2016", 9 pgs.
"U.S. Appl. No. 15/008,057, Reply Brief filed Oct. 2, 2018", 5 pgs.
"U.S. Appl. No. 15/008,057, Response filed May 24, 2017 to Final Office Action dated Nov. 25, 2016", 14 pgs.
"U.S. Appl. No. 15/008,057, Response filed Aug. 9, 2016 to Non Final Office Action dated May 9, 2016", 11 pgs.
"U.S. Appl. No. 15/936,635, Final Office Action dated Dec. 31, 2018", 14 pgs.
"U.S. Appl. No. 15/936,635, Non Final Office Action dated Jun. 5, 2020", 17 pgs.
"U.S. Appl. No. 15/936,635, Non Final Office Action dated Aug. 24, 2018", 14 pgs.
"U.S. Appl. No. 15/936,635, Notice of Allowance dated Aug. 28, 2020", 8 pgs.
"U.S. Appl. No. 15/936,635, Preliminary Amendment filed Mar. 27, 2018", 9 pgs.
"U.S. Appl. No. 15/936,635, Response filed Jan. 6, 2020 to Non Final Office Action dated Jun. 5, 2020", 13 pgs.
"U.S. Appl. No. 15/936,635, Response filed Jun. 26, 2019 to Final Office Action dated Dec. 31, 2018", 13 pgs.
"U.S. Appl. No. 15/936,635, Response filed Nov. 26, 2018 to Non Final Office Action dated Aug. 24, 2018", 15 pgs.
"U.S. Appl. No. 17/133,111, Non Final Office Action dated Apr. 21, 2021", 18 pgs.
"U.S. Appl. No. 17/133,111, Preliminary Amendment filed Apr. 17, 2021", 9 pgs.
"U.S. Appl. No. 17/133,111, Preliminary Amendment filed Dec. 23, 2020", 8 pgs.
"U.S. Appl. No. 17/133,111, Response filed Jul. 21, 2021 to Non Final Office Action dated Apr. 21, 2021", 14 pgs.
"U.S. Appl. No. 17/246,353, Notice of Allowance dated Oct. 6, 2021", 11 pgs.
"U.S. Appl. No. 17/246,353, Preliminary Amendment filed Jun. 25, 2021", 8 pgs.
"U.S. Appl. No. 17/246,353, Response filed Sep. 15, 2021 to Restriction Requirement dated Jul. 16, 2021", 6 pgs.
"U.S. Appl. No. 17/246,353, Restriction Requirement dated Jul. 16, 2021", 6 pgs.
"European Application Serial No. 14716029.5, Intention to Grant dated Aug. 10, 2016", 55 pgs.
"European Application Serial No. 16201115.9, Communication Pursuant to Article 94(3) EPC dated Mar. 15, 2021", 3 pgs.
"European Application Serial No. 16201115.9, Communication Pursuant to Article 94(3) EPC dated Jul. 22, 2020", 5 pgs.
"European Application Serial No. 16201115.9, Communication Pursuant to Article 94(3) EPC dated Oct. 29, 2019", 4 pgs.

(56) References Cited

OTHER PUBLICATIONS

"European Application Serial No. 16201115.9, Noting of Loss of Rights mailed Mar. 20, 2018", 1 pg.
"European Application Serial No. 16201115.9, Response filed Apr. 19, 2018 to Extended European Search Report dated Jun. 14, 2017", 5 pgs.
"European Application Serial No. 16201115.9, Response filed Apr. 28, 2020 to Communication Pursuant to Article 94(3) EPC dated Oct. 29, 2019", 7 pgs.
"European Application Serial No. 16201115.9, Response filed Sep. 15, 2021 to Communication Pursuant to Article 94(3) EPC dated Mar. 15, 2021", 58 pgs.
"European Application Serial No. 16201115.9, Response filed Nov. 25, 2020 to Communication Pursuant to Article 94(3) EPC dated Jul. 22, 2020", 5 pgs.
"European Application Serial No. 17198529.4, Communication Pursuant to Article 94(3) EPC dated Aug. 19, 2020", 4 pgs.
"European Application Serial No. 17198529.4, Communication Pursuant to Article 94(3) EPC dated Nov. 6, 2019", 3 pgs.
"European Application Serial No. 17198529.4, Extended European Search Report dated Feb. 1, 2018", 9 pgs.
"European Application Serial No. 17198529.4, Intention to Grant dated Jun. 10, 2021", 52 pgs.
"European Application Serial No. 17198529.4, Response filed Jan. 14, 2021 to Communication Pursuant to Article 94(3) EPC dated Aug. 19, 2020", 23 pgs.
"European Application Serial No. 17198529.4, Response filed May 27, 2020 to Communication Pursuant to Article 94(3) EPC dated Nov. 6, 2019", 8 pgs.
"European Application Serial No. 17198529.4, Response filed Sep. 21, 2018 to Extended European Search Report dated Feb. 1, 2018", 6 pgs.
"European Application Serial No. 17198610.2, Communication Pursuant to Article 94(3) EPC dated Jun. 8, 2021", 3 pgs.
"European Application Serial No. 17198610.2, Communication Pursuant to Article 94(3) EPC dated Aug. 19, 2020", 4 pgs.
"European Application Serial No. 17198610.2, Communication Pursuant to Article 94(3) EPC dated Nov. 6, 2019", 4 pgs.
"European Application Serial No. 17198610.2, Extended European Search Report dated Feb. 1, 2018", 7 pgs.
"European Application Serial No. 17198610.2, Response filed Feb. 2, 2021 to Communication Pursuant to Article 94(3) EPC dated Aug. 19, 2020", 4 pgs.
"European Application Serial No. 17198610.2, Response filed May 28, 2020 to Communication Pursuant to Article 94(3) EPC dated Jun. 11, 2019", 5 pgs.
"European Application Serial No. 17198610.2, Response filed Sep. 26, 2018 to Extended European Search Report dated Feb. 1, 2018", 4 pgs.
"European Application Serial No. 17198610.2, Response filed Oct. 7, 2021 to Communication Pursuant to Article 94(3) EPC dated Jun. 8, 2021", 45 pgs.
"International Application Serial No. PCT/IE2014/000005, International Preliminary Report on Patentability dated Jul. 16, 2015", 10 pgs.
"Japanese Application Serial No. 2015-562546, Amendment filed Feb. 24, 2017", with English translation, 6 pages.
"Japanese Application Serial No. 2015-562546, Notification of Reasons for Refusal dated May 29, 2018", with English translation, 6 pages.
"Japanese Application Serial No. 2015-562546, Notification of Reasons for Refusal dated Dec. 19, 2017", with English translation, 6 pages.
"Japanese Application Serial No. 2015-562546, Response filed May 18, 2018 to Notification of Reasons for Refusal dated Dec. 19, 2017", with English translation, 13 pages.
"Japanese Application Serial No. 2015-562546, Response filed Aug. 24, 2018 to Notification of Reasons for Refusal dated May 29, 2018", with English translation, 12 pages.
"Japanese Application Serial No. 2018-212388, Notification of Reasons for Refusal dated Dec. 24, 2019", with English translation, 7 pages.
"Japanese Application Serial No. 2018-212388, Response filed Jun. 24, 2020 to Notification of Reasons for Refusal dated Dec. 24, 2019", with English translation, 10 pages.
"Japanese Application Serial No. 2020-151484, Notification of Reasons for Refusal dated Sep. 14, 2021", with English translation, 6 pages.
"U.S. Appl. No. 17/246,353, Notice of Allowance dated Oct. 27, 2021", 2 pgs.
"U.S. Appl. No. 17/246,353, Notice of Allowance dated Nov. 10, 2021", 7 pgs.
"U.S. Appl. No. 17/133,111, Final Office Action dated Nov. 16, 2021", 21 pgs.
"European Application Serial No. 17198529.4, Indication of deficiencies in a request under Rule 22 EPC dated Oct. 19, 2021", 2 pgs.
"Japanese Application Serial No. 2020-151484, Notification of Reasons for Refusal dated Jan. 4, 2022", with English translation, 6 pages.
"Japanese Application Serial No. 2020-151484, Response filed Dec. 13, 2021 to Notification of Reasons for Refusal dated Sep. 14, 2021", with English claims, 6 pages.
"Japanese Application Serial No. 2020-151485, Response filed Dec. 13, 2021 to Notification of Reasons for Refusal dated Sep. 14, 2021", with English claims, 7 pages.

\* cited by examiner

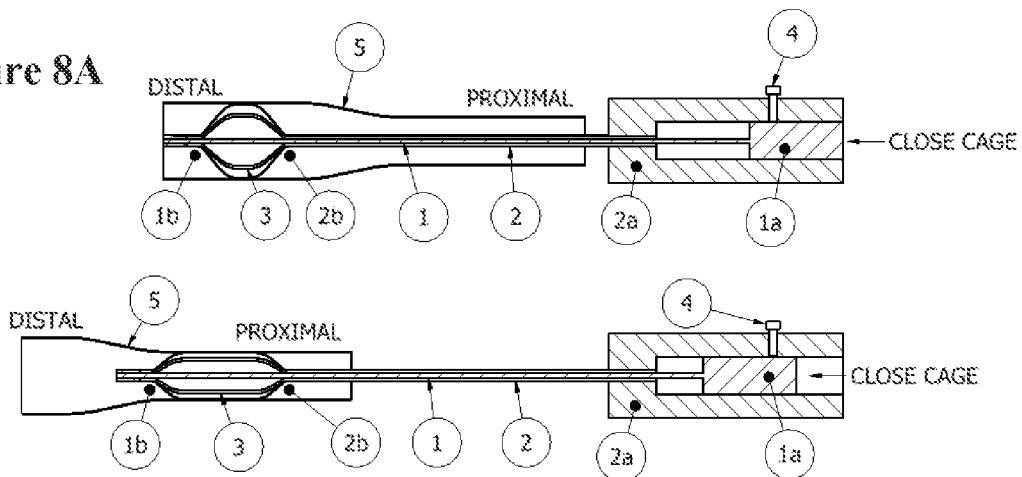
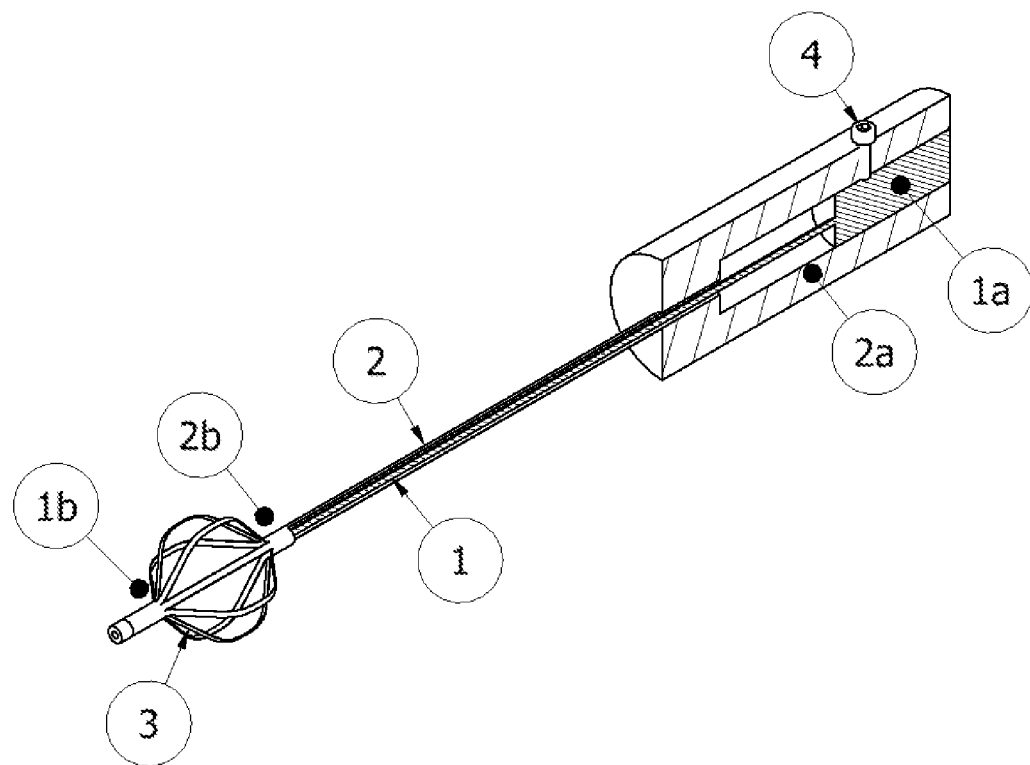

THROMBECTOMY DEVICES WITH ASPIRATION

CROSS-REFERENCE TO RELATED APPLICATIONS

This application is a continuation of U.S. application Ser. No. 17/133,111, filed Dec. 23, 2020, which is a continuation of U.S. application Ser. No. 15/936,635, filed Mar. 27, 2018, which is a continuation of U.S. application Ser. No. 15/008,057, filed Jan. 27, 2016, which is a continuation of U.S. application Ser. No. 14/776,633, filed Sep. 14, 2015, which is the U.S. national phase entry under 35 U.S.C. § 371 of PCT Application No. PCT/IE2014/000005, filed on Mar. 18, 2014, which claims priority to European Application No. 13159640.5, filed on Mar. 15, 2013, the entireties of each of which are incorporated by reference herein.

TECHNICAL FIELD

The invention relates to a device suitable for removing matter from inside the lumen and the wall of a body lumen. In particular, the invention relates to a thrombectomy device for removing thrombus from the walls of a vein or artery of a human.

BACKGROUND TO THE INVENTION

There have been many methods and devices to extract a blockage from vessels. Thrombectomy devices exist that macerate and extract the clot rather than pulling out the clot intact. The followings are some of the related patents.

U.S. Pat. No. 5,972,019 introduces an embolism treatment device having a core element and a cage. The cage may include an expandable braid which is rotatably attached to the core element and can be opened to separate the clot from the vessel wall or be expanded beyond the clot to pull it out. The core element has a rotatable part which is non removable from the cage.

U.S. Pat. No. 6,066,158 discloses an embolectomy device having a core wire element and a spiral collector to collect the embolism. The device may also have an actuator to allow expansion of the cage after delivery.

U.S. Pat. No. 5,795,322 presents a device for reducing the size of thrombus and removing it from the vessel. The device is a tube-like catheter with a filter formed from longitudinal strip-shape of the catheter. The filter opens when the distal and the proximal sided are pushed towards each other respectively. The device comprises a jet flow and lumen to extract the clot.

U.S. Pat. No. 6,660,014 presents a catheter for removing occlusive material from vessel lumen. The catheter comprises a radially expandable positioning cage and a radially expandable macerator within the cage. The diameter of the cage is adjustable with predetermined unconstrained diameter. U.S. Pat. No. 6,454,775 discloses an expansible macerator.

Patent application US 2006/0229645 presents a radially expansible cage for the removal of hardened and aged thrombus from the vessel wall. The cage opening and closing is controlled at the proximal/user end by moving the cage ends closer together or further apart; this is done either manually, or with a threaded tube to define the radial expansion of the cage.

U.S. Pat. No. 6,383,205 presents a mechanism including a double filter device to extract the clot with minimum risk of embolism.

U.S. Pat. No. 6,616,679 is a vascular device for emboli and thrombus removal. It includes a blood permeable sac which collects the emboli and can be collapsed. This is a fast way to extract small emboli but for large clot the sac need to be extremely long.

In U.S. Pat. No. 6,652,548 a thrombectomy device has been claimed. The catheter based device comprises shearing members located at the distal ends of the catheter and the inner shearing member is rotatable.

U.S. Pat. Nos. 6,656,203, 7,083,633, 7,014,647, 6,558,405, EP1310219A3EP1310219B1, 20070173883, U.S. Pat. Nos. 6,179,859, 7,922,741 and US20110125181 are examples of different structures for embolic filters. The filter may be placed in the vessel prior to an operation such as stenting or PTCA. After the operation, the filter is collapsed and taken out of the body. Neither of the filters are suitable for large tapered veins with thrombosis. Because filters are not designed to be moved along vessels after deployment, this makes it difficult to remove long thrombus. The existing devices and methods described above do not have a high performance in harvesting large volumes of thrombus and also thrombus in large and/or tapered and/or branched vessels. Limitations associated with these devices include procedural duration and thrombus removal efficiency.

It is an object of the invention to overcome at least one of the above-referenced problems.

STATEMENTS OF INVENTION

Broadly, the invention provides a device suitable for use in a body lumen comprising an elongated control member and a radially expansible member (i.e. a cage, funnel, or a ring) disposed at or adjacent to a distal end of the elongated control arm and that is adjustable between a contracted orientation and an expanded (deployed) orientation. The radially expansible member is adapted to remove matter (i.e. thrombus) from the walls of a body lumen (i.e. veins, arteries or other lumens such as the urethra), for example scrape thrombus from vessel walls, collect matter removed from the walls of a lumen, and optionally both, when in a deployed orientation. The control member comprises two arms, one of which is connected to or adjacent to a proximal end of the radially expansible member and the other of which is connected to or adjacent to a distal end of the radially expansible member. Movement of one of the arms relative to the other effects adjustment of the diameter or radial strength of the radially expansible member, for example adjustment of the diameter from a contracted orientation to an expanded (deployed) orientation, or adjustment of the radial force from a first force to a greater force. The movement is preferably longtitudinal movement. The device additionally includes a control mechanism that is ideally operatively connected to both arms and provides resistance to movement of one of the arms relative to the other. The control mechanism may comprise biasing means for biasing the radially expansible member into, or in the direction of, an expanded or contracted orientation (FIG. 11), it may include brake means which clamp the two arms in one orientation with a certain force such that movement of one of the arms relative to the other only occurs when a specific predetermined force is applied to the radially expansible member (FIG. 9), or it may comprise a combination of biasing means and brake means (FIG. 12).

A device of the invention is ideally suited for use in tapering lumens with obstructions such as valves where movement of the cage in a deployed shape along the lumen requires the diameter of the cage to change. When the lumen is tapering inwardly (in the direction of travel of the cage), the control mechanism exerts a force on the radially expansible member resisting contraction of the radially expansible member (by biasing the radially expansible member into an expanded orientation or by clamping the two arms in a specific disposition) until the force exerted on the radially expansible member by the lumen exceeds the total resistance force including that exerted by the resistance mechanism at which point the diameter of the radially expansible member will reduce. This means that the radially expansible member can be moved along the walls of the lumen exerting radial force against the walls, thereby effecting a scraping/collecting action.

Likewise, when the tube is tapering outwardly (in the direction of travel of the cage), the resistance mechanism comprises biasing means that exerts a force on the cage by biasing the cage into an expanded orientation. This means that cage will scrape along the walls of the vasculature exerting radial force against the walls, thereby effecting a scraping action along the outwardly tapering walls.

According to the invention, there is provided a device suitable for use in a body lumen and comprising:
- an elongated control member having a distal and a proximal end, and a radially expansible member disposed at or near the distal end and adapted for collection and/or shearing of matter from a wall of the body lumen,
- the radially expansible member having a proximal end and a distal end and being adjustable between a contracted orientation and an expanded orientation,
- the elongated control member comprising a proximal arm connected to the radially expansible member and a distal arm connected to the radially expansible member distally of the proximal arm connection such that movement of one arm relative to the other arm effects adjustment of the diameter and/or radial strength of the radially expansible member, the device being characterised in that it comprises a control mechanism operatively connected to both arms and adapted to provide resistance to the movement of one arm relative to the other.

The distal arm is generally connected to the radially expansible member distally of the proximal arm connection. Thus, the distal arm may be connected at or adjacent to the distal end of the radially expansible member, and the proximal arm may be connected to the radially expansible member at a point between the distal arm connection and the proximal end of the cage.

Preferably, the radially expansible member is a cage, although other radially expansible members such as, for example, expansible rings, funnels are envisaged. The radially expansible member may be formed from one, two, or more struts, which may be arranged in a helical arrangement to form the cage.

The distal or proximal arm may be, for example, a wire or a tube. In one embodiment, one of the arms is a tube (for example the proximal arm) and the other arm (for example the distal arm) is a wire, in which the wire is suitably disposed within a lumen in the tube. Suitably, the distal and proximal arms are co-extensive along most of their length (for example they are coextensive up to the cage). The control member comprising the two arms may be disposed within a tube, typically a catheter tube. In a preferred embodiment, the proximal arm is tubular and the distal arm is disposed within the proximal arm. Preferably, the distal arm is tubular (so as to facilitate the device being delivered over a guidewire).

Typically, the control mechanism comprises biasing means adapted to bias the radially expansible member into, or in the direction of, the expanded or contacted orientation. Ideally, the control mechanism comprises biasing means adapted to bias the cage into, or in the direction of, the expanded orientation.

Suitably, the control mechanism comprises brake means adapted to resist movement of one arm relative to the other arm. One embodiment of a brake means is a friction screw, typically an adjustable friction screw. Preferably, the control mechanism is adjustable so that the level of resistance to movement can be adjusted.

In one embodiment, the control mechanism comprises biasing means adapted to bias the radially expansible member into, or in the direction of, the expanded or contacted orientation and brake means adapted to resist movement of one arm relative to the other arm, for example brake means adapted to prevent expansion or retraction of the radially expansible member.

Suitably, the control mechanism comprises a first part connected to one of the arms, a second part connected to the other of the arms and movable relative to the first part, and force controlled resistance means for resisting movement of the first part relative to the second part. The force controlled resistance means may be biasing means adapted to bias the cage into, or in the direction of, the expanded or contacted orientation, and/or brake means adapted to resist movement of the radially expansible member or movement or one arm relative to the other arm, typically both.

In this specification, the term "force controlled" as applied to the resistance mechanism should be understood to mean that the diameter of the radially expansible member is not predetermined or controlled, but is dependent on the force applied.

In one preferred embodiment, the invention provides a device suitable for use in a body lumen and comprising:
- an elongated control member having a distal and a proximal end, and a radially expansible member disposed at or near the distal end and adapted for collection and/or shearing of matter from a wall of the body lumen,
- the radially expansible member having a proximal end and a distal end and being adjustable between a contracted orientation and an expanded orientation,
- the elongated control member comprising a proximal arm connected to the radially expansible member and a tubular distal arm connected to the radially expansible member distally of the proximal arm connection such that movement of one arm relative to the other arm effects adjustment of the diameter and/or radial strength of the radially expansible member,
- a control mechanism operatively connected to both arms and adapted to provide resistance to the movement of one arm relative to the other, in which the control mechanism comprises a first part connected to one of the arms, a second part connected to the other of the arms that is movable relative to the first part, and force controlled resistance means for resisting movement of the first part relative to the second part, characterised in that the force controlled resistance means comprises (a) biasing means for biasing the radially expansible member into the expanded orientation, or (b) a brake means adapted to resist movement of one of the first and second parts relative to the other of the first and second parts.

In another embodiment, the invention provides a device suitable for use in a body lumen and comprising:
- an elongated control member having a distal and a proximal end, and a radially expansible member disposed at or near the distal end and adapted for collection and/or shearing of matter from a wall of the body lumen, the radially expansible member having a proximal end and a distal end and being adjustable between a contracted orientation and an expanded orientation, a thrombus extractor, at least a part of which is preferably disposed within the radially expansible member the elongated control member comprising a proximal arm connected to the radially expansible member and a distal arm connected to the radially expansible member distally of the proximal arm connection such that movement of one arm relative to the other arm effects adjustment of the diameter and/or radial strength of the radially expansible member, a control mechanism operatively connected to both arms and adapted to provide resistance to the movement of one arm relative to the other, in which the control mechanism comprises a first part connected to one of the arms, a second part connected to the other of the arms that is movable relative to the fixed first part, and force controlled resistance means for resisting movement of the first part relative to the second part, characterised in that the force controlled resistance means comprises (a) biasing means for biasing the radially expansible member into the expanded orientation, or (b) a brake means adapted to resist movement of one of the first and second parts relative to the other of the first and second parts.

Typically, the force controlled resistance means comprises biasing means, for example a resiliently deformable or displacable member such as for example a spring or a pneumatic or hydraulic member, generally disposed between the first and second parts of the control mechanism. The spring may be any type of spring, for example a compression, tension, flat, constant force, or adjustable constant spring.

In one embodiment, the force controlled resistance means comprises biasing means, for example a resiliently deformable member disposed between the first and second parts of the resistance mechanism, and a brake means adapted or configured to resist movement of one of the first and second parts relative to the other of the first and second parts.

The control mechanism may be disposed at any point along the device, for example proximal to the radially expansible member, distal to the radially expansible member, or adjacent to or within the radially expansible member. In a preferred embodiment, the control mechanism is disposed at a proximal end of the catheter (for example, on the handle) such that, in use, it is exposed proud of the body.

In a preferred embodiment of the invention, the first part of the control mechanism is connected to the proximal end of the radially expansible member by means of the proximal arm, and the adjustable second part of the control mechanism is attached to the distal end of the radially expansible member by means of the distal arm. Thus, the distal arm typically passes through the cage.

Preferably, the proximal arm is a tube comprising a lumen and the distal arm is disposed within the lumen of the first arm, typically coaxially with the first arm. Preferably, the distal arm is a tube, ideally adapted for receipt of a guidewire.

Movement of one arm relative to the other arm effects adjustment of the diameter and/or radial strength of the radially expansible member. Preferably, the movement is longtitudinal movement, although other movement is envisaged, for example lateral, radial, circumferential rotational or combinations thereof.

In one embodiment, the brake means comprises a friction screw fixed to one of the parts of the control means and adjustable to engage the other part of the control means (or the arm that is operably connected to the other part). Preferably, the friction screw is fixed to the second part, for example a movable stop forming part of the second part, and is adjustable to engage the first part or the control means or the distal arm that is operable connected to the first part.

In one embodiment of the control mechanism, the first part comprises a barrel, and the second part is adapted for sliding movement within the barrel, wherein the resistance means comprises a friction screw, preferably an adjustable friction screw, disposed on the barrel and adapted for engagement with the second part. Suitably, the resistance means additionally comprises biasing means suitably adapted to bias the cage into, or in the direction of, the expanded orientation.

Typically, the control mechanism is disposed proximally of the radially expansible member such that in use it is located outside of the body. Suitably, the first part is operably connected to the proximal arm and comprises a guide path, and the second part is operably connected to the distal arm and is associated with the first part for movement along the guide path, and wherein the force controlled resistance means comprises a resiliently deformable member disposed along the guide path between the first and second parts. Preferably, the first part comprises a barrel and a second part comprises a block configured for sliding and controlled movement within the barrel.

Typically, the first part comprises a movable stop which is movable to vary the length of the guide path and/or the resiliently deformable member.

Suitably, the brake means comprises a friction screw operably connected to the movable stop and configured for adjustable engagement with the distal arm.

Suitably, the control mechanism is disposed within the radially expansible member and comprises a first part connected to the distal arm, a second part connected to the proximal arm, and a helical spring operatively connected to the first and second parts and configured to provide force controlled resistance to movement of the first and second parts together.

Preferably, the radially expansible member comprises a cage. Suitably, the cage comprises a proximal portion having apertures for receipt of thrombus into the cage, and a distal portion having a fine mesh for capturing thrombus, in which the cage optionally comprises a cut tube. Alternatively, the cage comprises a distal portion having apertures for receipt of thrombus into the cage, and a proximal portion having a fine mesh for capturing thrombus, in which the cage optionally comprises a cut tube.

Suitably, the control mechanism is disposed distally of the radially expansible member. Suitably, the control mechanism comprises a resiliently deformable member (i.e a spring) having a distal end (first part) operably connected to the distal arm and a proximal end (second part) operably connected to a distal end of the radially expansible member, and wherein the distal end of the distal arm is operably connected to the distal end of the radially expansible member by means of the resiliently deformable member.

Preferably, the device comprises an extractor at least a part of which is disposed within the radially expansible member. Suitably, the extractor comprises holes or apertures dimensioned to allow blood, but prevent thrombus, pass out of the extractor.

Suitably, the extractor comprises a helical formation adapted to rotate. The rotation is adapted to remove thrombus from the radially expansible member or optionally deliver agents into the body lumen, for example a thrombolytic agent. The helical formation may comprises a single, double or triple helical formation. Typically, the pitch of the helix on the helical formation is configured to squeeze blood from thrombus during use.

Typically, the helical formation is disposed within an extractor tube. Ideally, a portion of the helical formation within the radially expansible member is exposed by means of, for example, one or more windows or cut-away portions.

Suitably, a leading edge of the extractor tube comprises a cutting edge. Preferably, the helical formation comprises a cutting edge, ideally disposed at or adjacent a distal end of the helical formation. In one embodiment, a leading edge of the extractor tube comprises a cutting edge and the extractor comprises an aspirator tube.

In one embodiment, the thrombus extractor is an aspirator tube.

Typically, the force controlled resistance means is self-adjusting. In this specification, the term "self adjusting" as applied to the force controlled resistance means should be understood to mean that the resistance means adjusts itself without any user input other than the actions of the user to move the device along a vessel.

Typically, the elongated control member is contained within a tubular sheath. Ideally the tubular sheath extends along all or most of the length of the control member. Suitably, the longtitudinal position of the sheath is adjustable. Suitably, the tubular sheath can be adjusted to cover the radially expansible member and maintain the radially expansible member in a contracted orientation.

Typically, the tubular sheath comprises a plurality of holes for perfusion of a liquid.

Suitably, the device comprises a liquid administration lumen configured to deliver a liquid into the body. Preferably, the liquid administration lumen comprises a lumen formed within the distal arm, between the distal arm and proximal arm, and between the proximal arm and an external sheath. Ideally, the device comprises an injection port for delivery of liquid into the liquid administration lumen. In a preferred embodiment, the invention provides a device suitable for use in a body lumen and comprising:

an elongated control member having a distal and a proximal end, and a radially expansible member disposed at or near the distal end and adapted for collection and/or shearing of matter from a wall of the body lumen, the radially expansible member having a proximal end and a distal end and being adjustable between a contracted orientation and an expanded orientation, the elongated control member comprising a proximal arm connected to the radially expansible member and a distal arm connected to the radially expansible member distally of the proximal arm connection such that movement of one arm relative to the other arm effects adjustment of the diameter or radial strength of the radially expansible member, the device being characterised in that it comprises biasing means for biasing the radially expansible member into, or in the direction of, an expanded orientation.

In another embodiment, the invention provides a device suitable for use in a body lumen and comprising:

an elongated control member having a distal and a proximal end, and a radially expansible member disposed at or near the distal end and adapted for collection and/or shearing of matter from a wall of the body lumen, the radially expansible member having a proximal end and a distal end and being adjustable between a contracted orientation and an expanded orientation, the elongated control member comprising a proximal arm connected to the radially expansible member and a distal arm connected to the radially expansible member distally of the proximal arm connection such that movement of one arm relative to the other arm effects adjustment of the diameter or radial strength of the radially expansible member, the device being characterised in that it comprises biasing means for biasing the radially expansible member into, or in the direction of, an expanded orientation and brake means brake means adapted to resist movement of one arm relative to the other arm.

In another embodiment, the invention provides a device suitable for use in a body lumen and comprising:

an elongated control member having a distal and a proximal end, and a radially expansible member disposed at or near the distal end and adapted for collection and/or shearing of matter from a wall of the body lumen, the radially expansible member having a proximal end and a distal end and being adjustable between a contracted orientation and an expanded orientation, the elongated control member comprising a proximal arm connected to the radially expansible member and a distal arm connected to the radially expansible member distally of the proximal arm connection such that movement of one arm relative to the other arm effects adjustment of the diameter or radial strength of the radially expansible member, the device being characterised in that it comprises a resistance mechanism comprising a fixed first part connected to one of the arms, a second part connected to the other of the arms and movable relative to the fixed first part, and resistance means for resisting movement of the first part relative to the second part, in which the resistance means optionally comprises biasing means adapted to bias the cage into the expanded or contacted orientation or brake means adapted to prevent expansion of the cage.

In one embodiment, the radially expansible member is a cage. Typically, the cage is a filtering cage (i.e. it is adapted to collect or filter thrombus from blood that passes through the cage). In another embodiment, the cage is a shearing cage (i.e. a cage adapted to shear or scrape thrombus from a wall of the vasculature). In a preferred embodiment, the cage is both a shearing and filtering cage. Suitably, the cage has a proximal end that is at least partially open (for receipt of thrombus). The cage may comprise a braided material, for example a braided wire, or it may comprise a cut tube, for example a cut tube (i.e. Polymeric, metal such as stainless steel Nitinol or cobalt chromium, or ceramic; or a combination of these materials) or a laser cut tube, or it may comprise a braided material and a cut tube. When formed from a braided material, the density of the braid may be greater towards the distal end of the cage that the proximal end of the cage. In a preferred embodiment, the cage is formed from a shape memory material such as Nitinol. Preferably, the cage has an at least partially open proximal end and tapers inwardly towards its distal end.

In one embodiment, the cage comprises a distal section having a fine mesh, and an intermediate section having large apertures. Thus, the fine mesh is suited for filtering/capturing thrombus, and the large apertures adapted for allowing passage into the cage of thrombus. Typically, the cage is cut from a tube, suitably a polymeric or metal tube.

In one embodiment, the cage comprises a cutting element disposed circumferentially around the cage. This may be a wire, or a cutting edge. Typically, at least a part of the cutting element is exposed proud of the cage. Suitably, at least a part of the cutting element is disposed within the cage. Typically, the cutting element is disposed with respect to the cage such that the cutting element expands and contracts with the expansion and contraction of the cage, respectively.

In one embodiment, the invention provides a device suitable for use in a body lumen and comprising:
- an elongated control member having a distal and a proximal end, and a cage disposed at or near the distal end and adapted for collection and/or shearing of matter from a wall of the body lumen,
- the radially expansible member having a proximal end and a distal end and being adjustable between a contracted orientation and an expanded orientation,
- the elongated control member comprising a proximal arm connected to the radially expansible member and a distal arm connected to the radially expansible member distally of the proximal arm connection such that movement of one arm relative to the other arm effects adjustment of the diameter or radial strength of the radially expansible member the device being characterised in that the cage comprises a distal section having a fine mesh for capturing thrombus, optionally a proximal section having a coarse mesh adapted for crimping attachment to the proximal arm, and an intermediate section having apertures dimensioned to allow passage of thrombus into the cage.

In another embodiment, the invention provides a device suitable for use in a body lumen and comprising:
- an elongated control member having a distal and a proximal end, and a cage disposed at or near the distal end and adapted for collection and/or shearing of matter from a wall of the body lumen,
- the cage having a proximal end and a distal end and being adjustable between a contracted orientation and an expanded orientation,
- the elongated control member comprising a proximal arm connected to the radially expansible member and a distal arm connected to the radially expansible member distally of the proximal arm connection such that movement of one arm relative to the other arm effects adjustment of the diameter or radial strength of the radially expansible member, the device being characterised in that the cage has an at least partially open proximal end and tapers inwardly towards its distal end, and wherein a helical extractor is optionally disposed within the cage towards a distal end of the cage.

In one embodiment, the invention provides a device suitable for use in a body lumen and comprising:
- an elongated control member having a distal and a proximal end, and a cage disposed at or near the distal end and adapted for collection and/or shearing of matter from a wall of the body lumen,
- the cage having a proximal end and a distal end and being adjustable between a contracted orientation and an expanded orientation,
- the elongated control member comprising a proximal arm connected to the radially expansible member and a distal arm connected to the radially expansible member distally of the proximal arm connection such that movement of one arm relative to the other arm effects adjustment of the diameter or radial strength of the radially expansible member, the device being characterised in that the cage comprises a cutting or seperation element disposed circumferentially around the cage.

Preferably, the device of the invention comprises an extractor for matter (i.e. debris such as thrombus) at least a part of which is preferably disposed within the radially expansible member. The extractor may comprise either aspiration, a helical formation adapted to rotate and remove thrombus from the radially expansible member, or a combination of both. The helical formation may comprise a screw or auger, that is preferably arranged co-axially about the second (distal) arm, but optionally may be arranged eccentrically to the radially expansible member axis. Alternatively, the helical formation may comprise a helical wire or the like arranged, for example, around the distal arm and adapted to rotate. Preferably, the helical formation is disposed within an extractor tube, wherein a distal end of the helical formation that is disposed within the cage is exposed proud of the extractor tube (i.e. the tube may be cut-away leaving a part of the helical formation within the radially expansible member exposed. In one embodiment of the invention, the extractor comprises a wire arranged helically about the distal arm for rotation about the arm, and an extractor tube, wherein the helical wire and distal arm are disposed within the extractor tube with a portion of the distal end of the helical wire exposed proud of the extractor tube. Suitably, the extractor tube comprises a window disposed within the cage, typically disposed towards the distal end of the cage. Preferably, a leading edge of the extractor tube comprises a sharp or cutting edge.

In the device of the invention, the proximal arm is generally connected at or adjacent to the proximal end of the radially expansible member. Typically, the distal arm is generally connected at or adjacent to the distal end of the radially expansible member.

Preferably, the device is a thrombectomy device, ideally a thrombectomy catheter.

The invention also relates to a method for removing matter from a target area of a wall of a body lumen, for example thrombus from a wall of a vein or artery, comprising a step of providing a device according to the invention with the radially expansible member is a contracted orientation, inserting the device into the target lumen such that the radially expansible member is positioned distally of the target area of the wall, adjusting the radially expansible member from a contracted orientation to an expanded (deployed) orientation, and withdrawing the radially expansible member along the lumen such that the radially expansible member scrapes some/all matter from the target area of the wall of the lumen.

The invention also provides a method of removing thrombus from a blood vessel comprising the steps of placing the device of the invention in a blood vessel, and moving the device along the blood vessel. Typically, the device is moved along the blood vessel in an inwardly tapering direction or an outwardly tapering direction. Suitably, the blood vessel is a vein, typically a large vein.

BRIEF DESCRIPTION OF THE FIGURES

The invention will be more clearly understood from the following description of some embodiments thereof, given by way of example only, in which:

FIGS. 8A and 8B. Schematic of the cage and control mechanism, operated using a friction screw.

FIG. 9. Schematic of the cage and control mechanism, operated using a friction screw.

DETAILED DESCRIPTION OF THE INVENTION

Cage and Filter

The cage can be made in many different ways, such as from a braid, a series of wires, laser cut tubes or a combination of them. The cage also may act as a filter or be a structure for the filter at the distal part. The cage can be made of different materials such as, but not limited to, polymeric, metal such as stainless steel Nitinol or cobalt chromium, or ceramic; or a combination of these materials. The proximal side of the cage is generally open and allows thrombus into the cage. The distal part of the cage is suitably constrained onto a tube or wire with small diameter and the proximal part of the cage is connected to a tube with larger diameter. A sheath may cover the entire device at delivery and at retrieval.

A connector, which can be a wire or tube and connects the distal end of the cage to user or controls the distal movement of the cage, is called the distal arm. Another connector, which can be a wire or tube and connects the proximal end of the cage to user, is called the proximal arm.

Once the cage is assembled and opened, section 202 provides a passageway for thrombus into the cage, while section 201 prevents large thrombus passing the cage (1).

Figure 2:
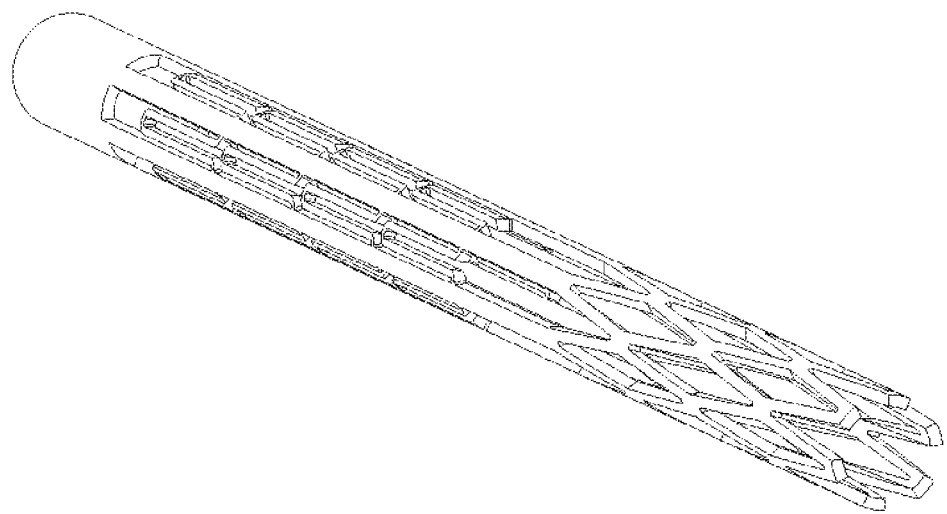
FIG. 2. An example of a cage made from laser cut Nitinol. The distal side is solid tube and the proximal side is a closed mesh to fit over the proximal arm tube.
Figure 3:
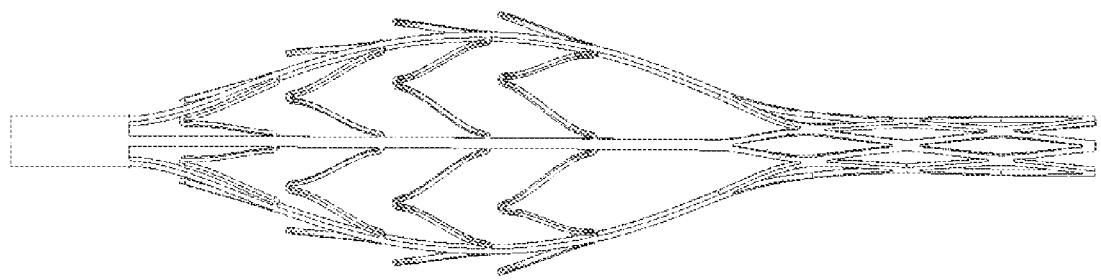
FIG. 3. An example of a laser cut cage after expansion. The circumferential elements act as filter and separate the thrombus from the vessel wall.

In FIGS. 2 and 3, an example of a cage which has been laser cut from Nitinol tube is shown. The laser cuts have the same feature as the braided mesh. It provides a passageway on the proximal side and acts as filter on the distal side. It may also carry circumferential elements for cutting through thrombus and separating thrombus from the wall.

By pushing the proximal and distal ends of the cage axially towards each other the diameter of the cage and its radial force may increase. By pulling the sides away from each other the diameter and the radial force of the cage may decrease.

Relative movement of the distal and proximal arms controls the distance between the distal and proximal sides of the cage; this adjusts the diameter and radial strength of the cage. If the distal arm is fixed and the proximal arm is pulled proximally by the user, the diameter of the cage becomes smaller. If the proximal arm is fixed and the distal arm is being pulled, the diameter of the cage increases.

Figure 4:
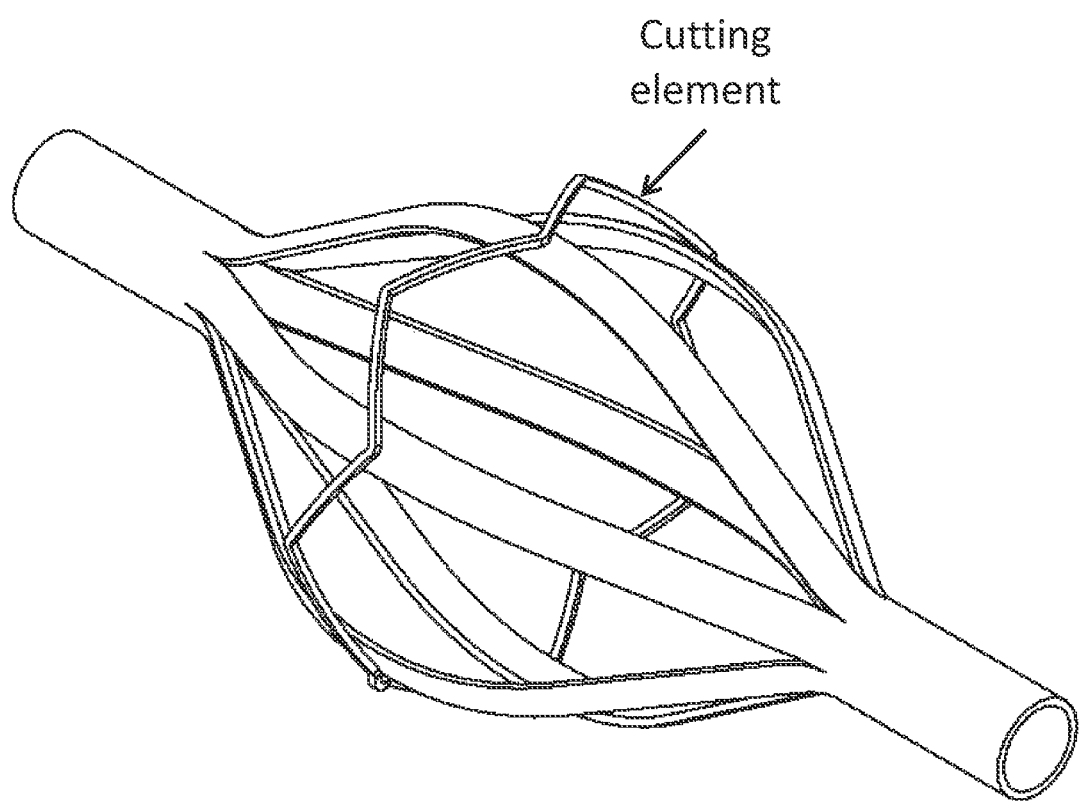
FIG. 4. Cage with cutting element external to the cage.
Figure 5:
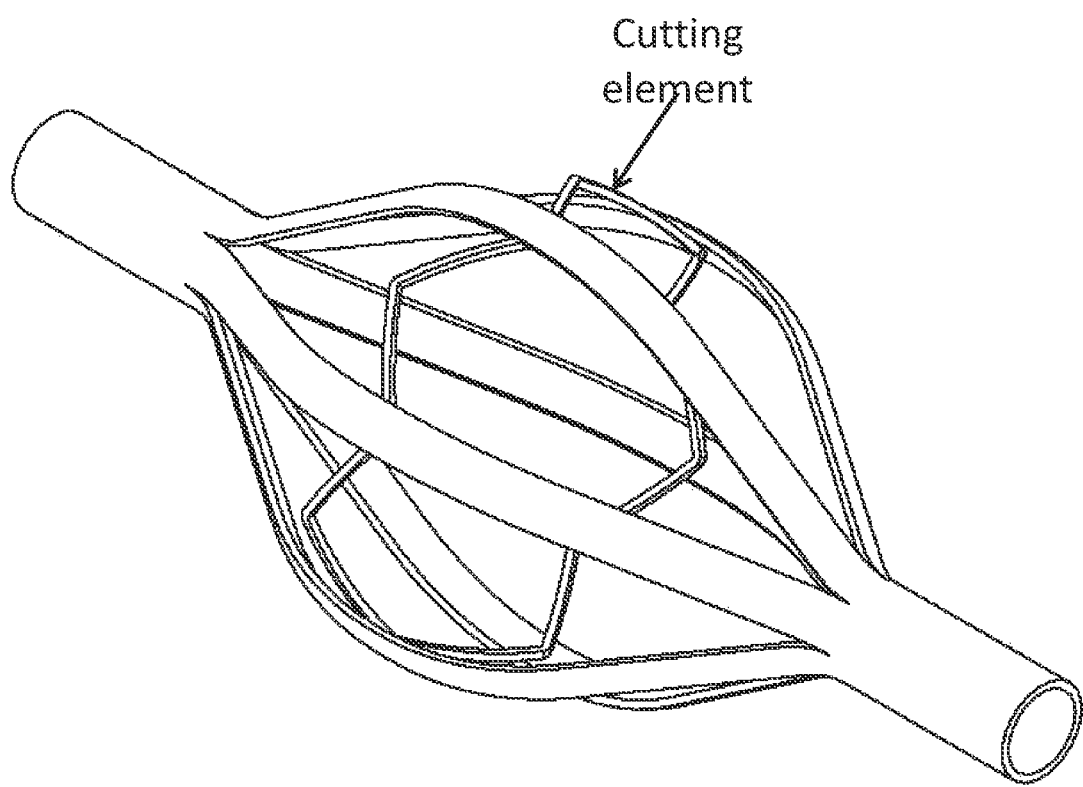
FIG. 5. Cage with cutting element internal to the cage.
Figure 6:
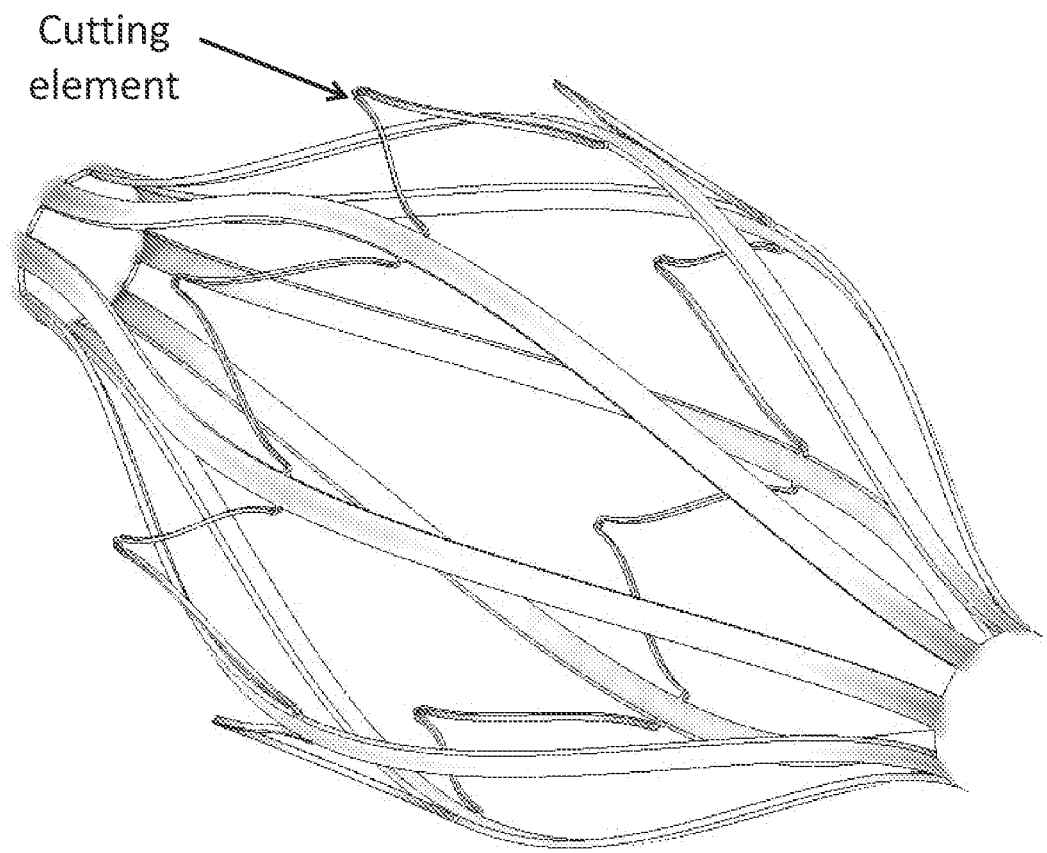
FIG. 6. Cage with cutting element as part of the cage.
Figure 7:
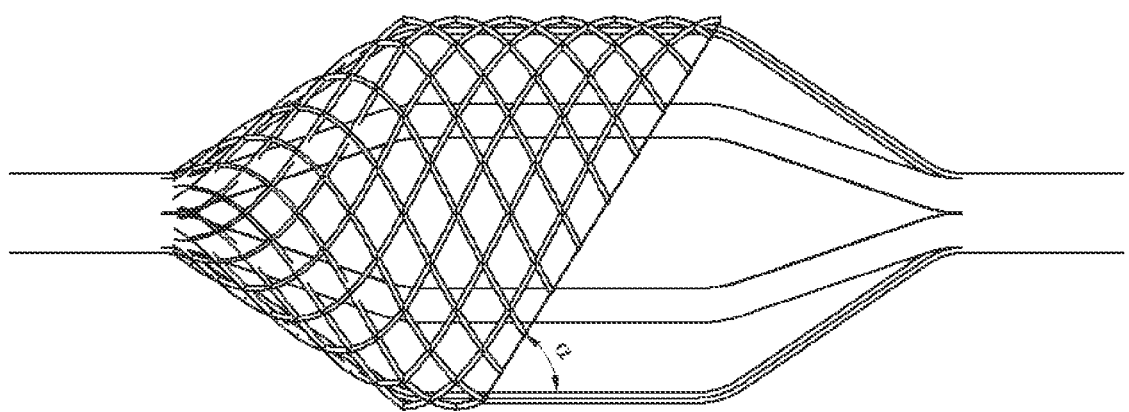
FIG. 7. The perimeter of the cage may be tapered at an angle.

The cage may also have a circumferential cutting element for removing/scraping thrombus from the vessel wall. This may be contained around or within the cage and may be composed of a round wire, flat wire, blade or a combination of these. FIG. 4 shows the cage with a flat wire attached the outside of the cage; the wire can scrape thrombus from the vessel wall. FIG. 5 shows the cutting element internal to the cage, while FIG. 6 shows the cutting element of the cage as one part (in this case from a laser cut tube). The cutting/scraping element may also be tapered at an angle (FIG. 7).

A Cage with Self Adjustable Diameter Control Mechanism

In the case of treating a tapered vessel, the cage diameter should be adjustable while it is pulled along the lumen. Also in the case of obstruction such as vascular valve it is desirable that the device be able to manoeuvre through it. Therefore a mechanism which can control the diameter of the cage by changing the resistance force is desirable. Presented here is a mechanism to control the diameter of the cage based on resistance forces.

As the cage moves through a reducing tapered vessel (pulling the proximal arm), the vessel exerts a force on the cage. When the force from the vessel exceeds the total force including the preset force from the resistance mechanism (set by the user), the distal arm moves distally relative to the proximal arm; this closes the cage. The next section includes some embodiments of the self-adjustment mechanisms.

The control mechanism may contain friction elements, springs, pneumatics, hydraulics, simple weight, or a combination of these elements.

Resistance Mechanism: Sliding

In this embodiment of the invention (FIGS. 8A, 8B, and 9), the cage (3) is made from a laser cut self-expanding tube. The cage opens when 1b and 2b move closer together, and closes when 1b and 2b move apart. The mechanism for controlling the diameter and force exerted by the cage on the vessel wall is the basis for the current invention.

The device, as shown in FIGS. 8A and 8B, consists of a cage (3) which has a distal end (1b) and a proximal end (2b), a distal arm (1), a proximal arm (2), and a handle. The control mechanism is comprised in the handle, and comprises a first part in the form of a housing (2a) having a guidance path, a second part in the form of a sliding block (1a) configured for sliding movement along the guidance path of the housing (2a). Force controlled resistance means is provided in the form of a brake adapted to resist movement of one or the arms relative to the other. In this embodiment, the brake comprises a friction screw (4) mounted on the housing (2a) and adjustable to apply a compression force against the sliding block (1a) to provide resistance to movement of one arm relative to the other, and in the case of the device being passed along a vessel that tapers inwardly, resistance to the compression of the cage which has the effect of keeping the periphery of the cage in contact with the vessel wall.

The process begins in an expanded state in the vessel as shown in FIG. 8A. The opening and closing of the cage is governed by the relative movement of the sliding block (1a) to the handle (2a). As the cage is pulled by the handle through an obstruction or the tapered section of the vessel (5), force from the vessel wall is exerted to the cage. This force is transferred to the sliding block (1a). If the force applied to the block 1a is larger than the preset friction force, then the block 1a slides forward from its position in FIG. 8A to its position in FIG. 8B. This allows the cage to conform to the shape of the narrower vessel. The force exerted by the cage on the vessel is therefore dictated in part by the ease of movement of the sliding block relative to the handle; this is controlled by the friction screw.

Resistance Mechanism: Sliding and Spring

Figure 10:
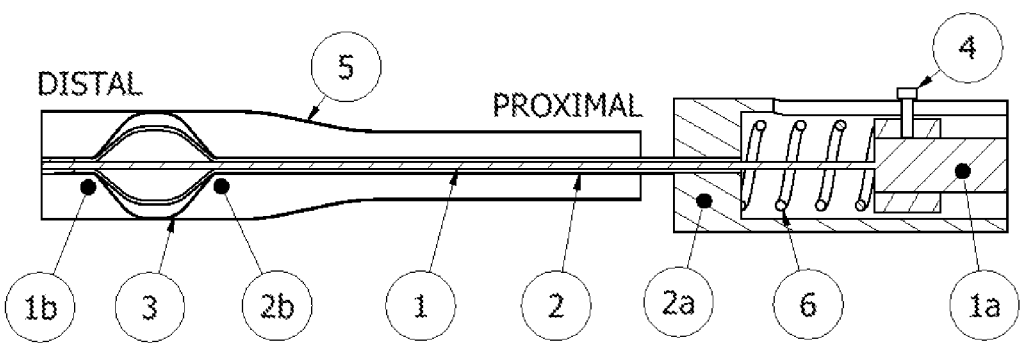
FIG. 10. Schematic of the cage and control mechanism, operated using a friction screw and a spring.
Figure 11A:
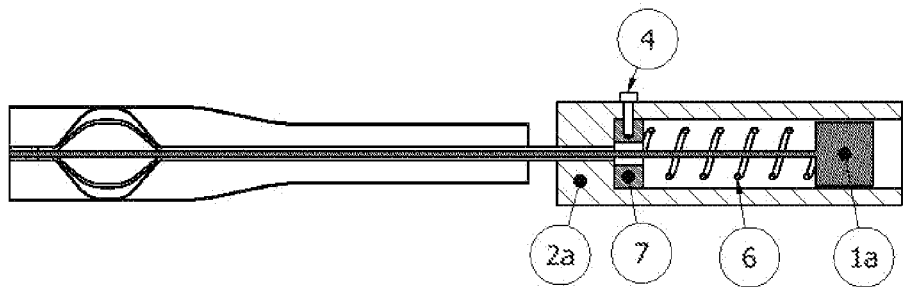
FIGS. 11A and 11B. Schematic of the cage and control mechanism, operated using a spring, and a movable stop.
Figure 11B:
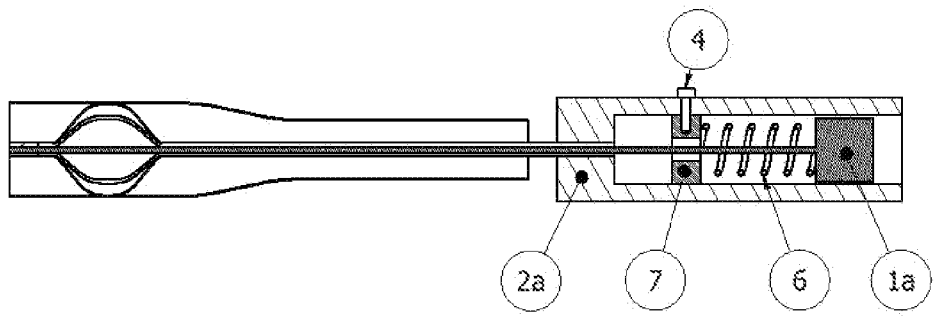

FIGS. 11A and 11B show an alternative embodiment of the resistance mechanism in which parts described with reference to FIG. 10 are assigned the same reference numerals. In this embodiment, a compression spring (6) is disposed along the guide path between the housing (2a) and the sliding block (1a). The housing (2a) is connected to the proximal arm (2) and the block (1a) is connected to the distal arm (1). Thus, compression of the cage (3) into a contracted orientation causes the distal arm (1) to extend, causing compression of the spring. In this manner, the cage is biased into an expanded orientation when it is being passed along a vessel that is narrowing, thereby maintaining contact between the cage and the vessel wall. A friction screw (4) is mounted on the housing (2a) and is adjustable to apply a compression force against the block (1a) and thereby provides further resistance to movement of one arm relative to the other, and in the case of the device being passed along a vessel that tapers inwardly, again provides resistance to the compression of the cage which has the effect of keeping the periphery of the cage in contact with the vessel wall.

FIGS. 11A and 11B show an alternative embodiment of the resistance mechanism in which parts described with reference to FIGS. 8 to 10 are assigned the same reference numerals. In this embodiment, the self adjusting mechanism comprises a movable stop (7) that is movable to adjust the length of the guidance path and, thus, the degree of compression of the spring. Thus, the force that the spring applies can be varied by changing the position of the movable stop (7) along the guidance path.

Resistance Mechanism: Spring With Adjustable Spring Constant

Figure 12:
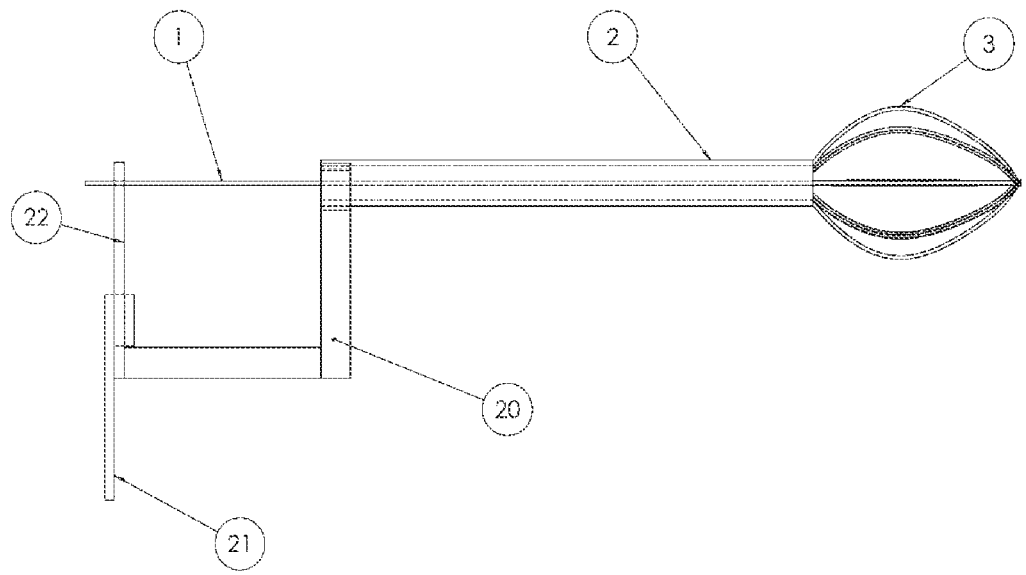
FIG. 12. Schematic of the cage and control mechanism, operated using a flat spring.
Figure 13:
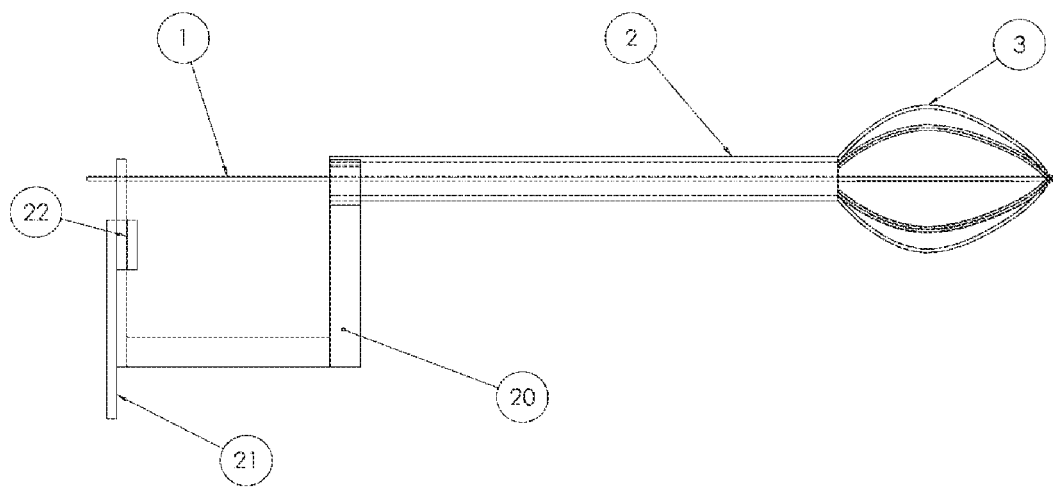
FIG. 13. Schematic of the cage and control mechanism, operated using a flat spring.
Figure 14:
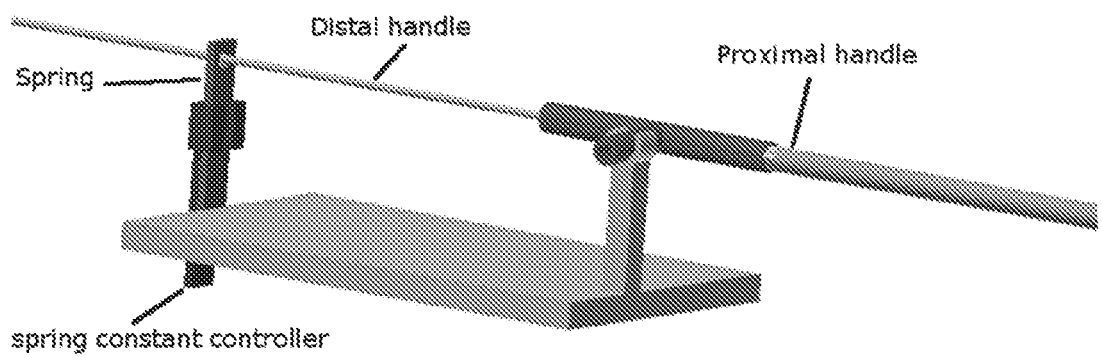
FIG. 14. Schematic of the control mechanism, operated using a flat spring.

In this embodiment the distal arm (1) is attached to a flat spring (22). The other side of the spring (22) is fixed respect to proximal arm (2) through a solid handle (20). Since the spring constant of a flat spring changes with its length, a mechanism for adjusting its length (21) can slide over the spring to control its deformation. When the sliding part (21) is down (FIG. 12) the spring constant is the lowest which means it allows higher displacement of inner tube (1) at a lower force. When the sliding tube (21) rises (FIG. 13), the spring constant (22) increases which allows less displacement of inner tube (1). This effectively reduces the cage diameter (3). FIG. 14 shows a 3D representation of the mechanism.

The Extraction Mechanism

Figure 1:
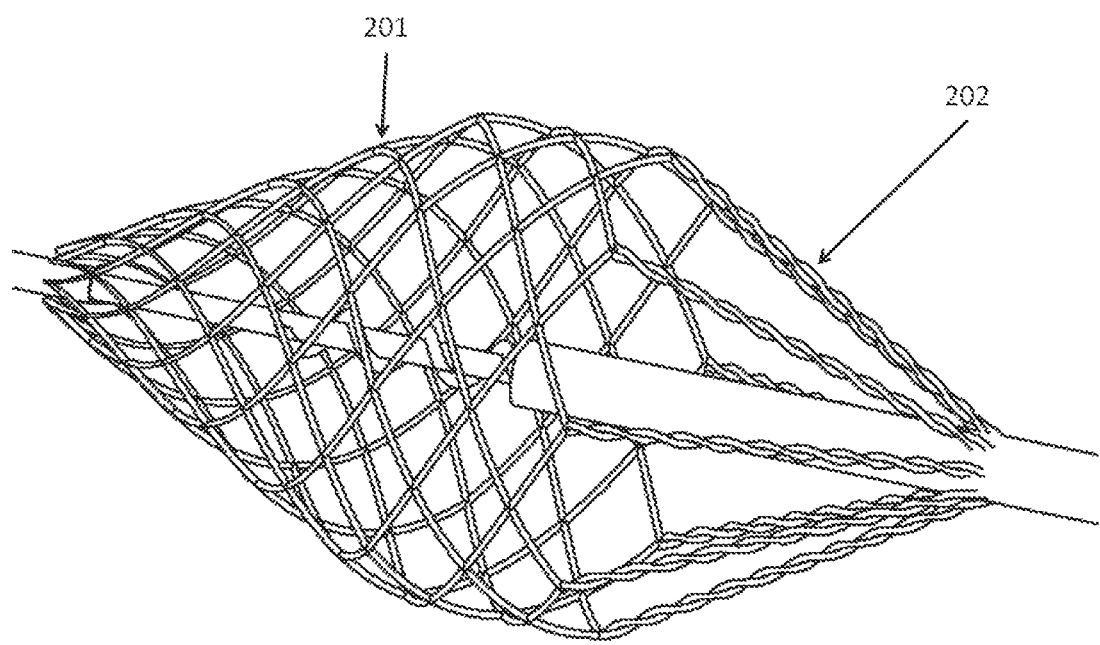
FIG. 1. Shows a braided cage in its expanded configuration, with a filtered end (201) and an open end (202).
Figure 15:
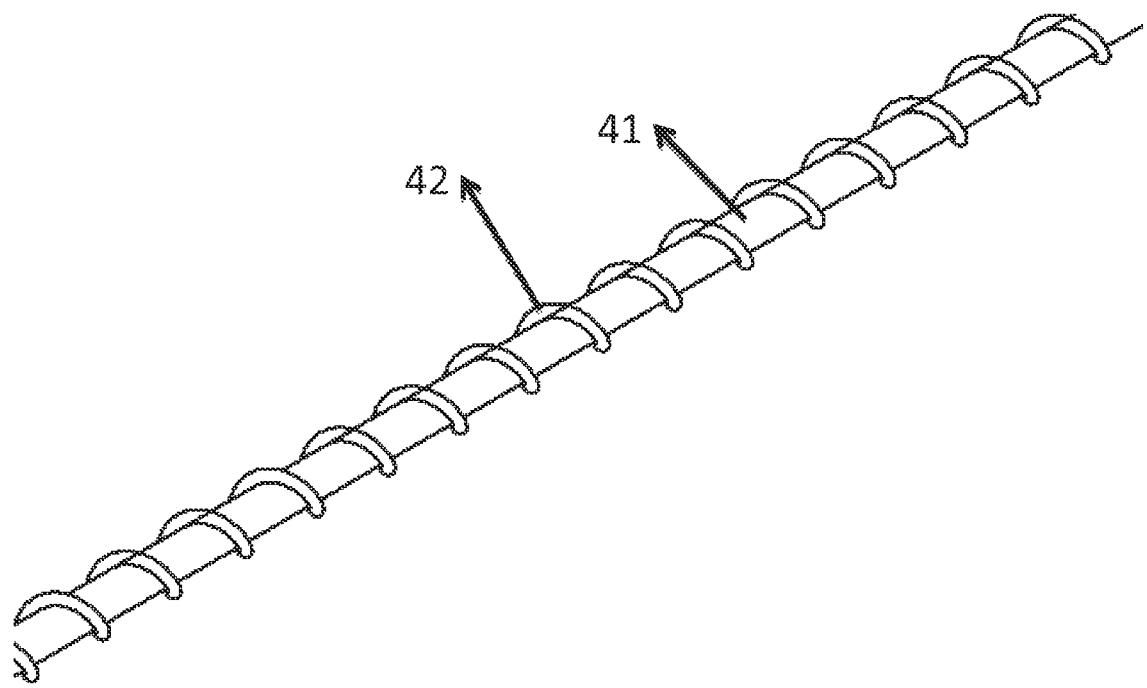
FIG. 15. The extractor is made of a wire wrapped around a tube. It transports and macerates the thrombus.

The extraction system may consist of suction, or a rotating tube/wire with a means of transformation and/or maceration on the outer surface; the extraction system may also contain a combination of these mechanisms. The rotating extractor may be manufactured from one part or made from several attachments. For example, the extraction mechanism may comprise a wire (42) wrapped around an extraction core tube (43) (FIG. 15). This tube may be placed over the distal arm (1) of the cage and inside the proximal arm (2). Alternatively, the distal arm may be used as the extraction core tube. The distal side of the extraction core tube may be close to the distal end of the proximal arm (2). As the extraction tube turns at high speed thrombus is forced proximally between the extraction tube and the proximal arm. The distal end of the extraction mechanism may be located inside the cage (FIG. 1).

Figure 16:
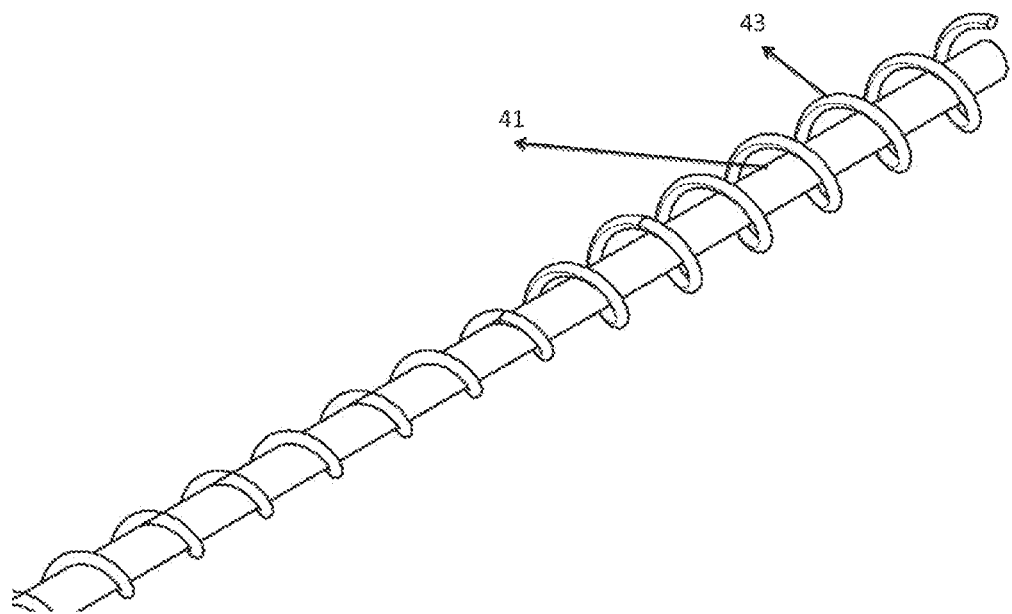
FIG. 16. The wire may be displaced above the tube surface.

The wire may have varying cross sections along the device for different means; from circular, rectangular or triangular cross sections. The wire can be from different materials such as stainless steel, Nitinol, or polymers. Once the wire is wrapped around the tube, it might be completely fit around the tube (41) or be partially fit at a distance (43) from the rotating tube (41) surface (FIG. 16).

Figure 17:
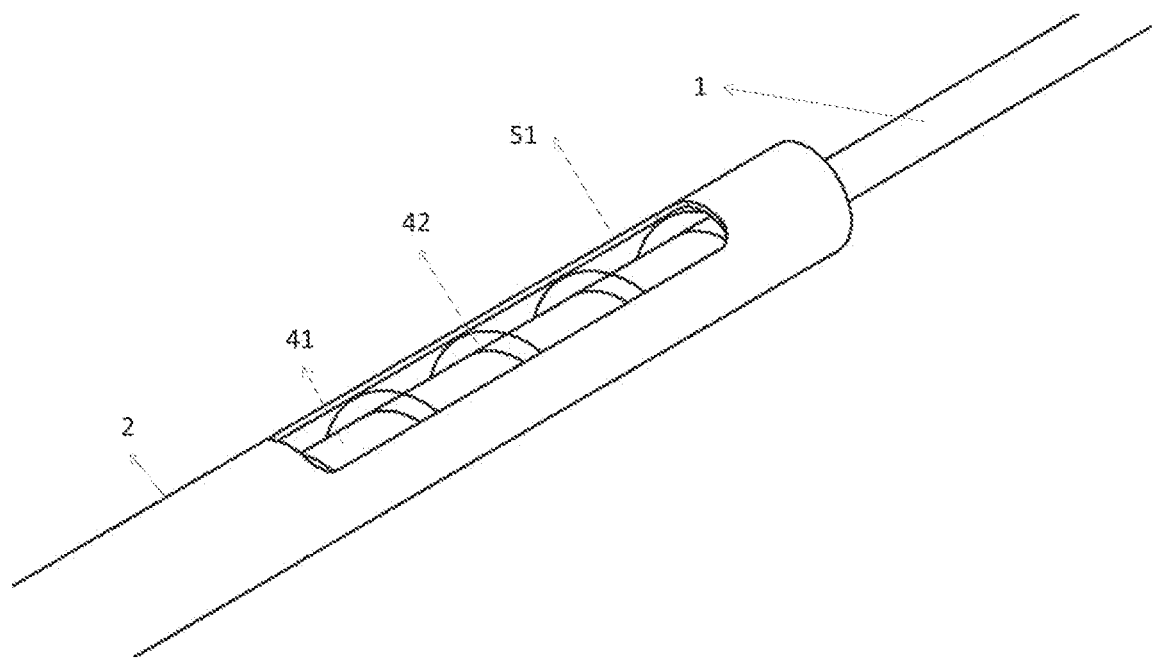
FIG. 17. The proximal arm may act as the outer tube of the extraction mechanism and provide a passage way to let material from the blood vessel into the lumen of the macerator.
Figure 18A:
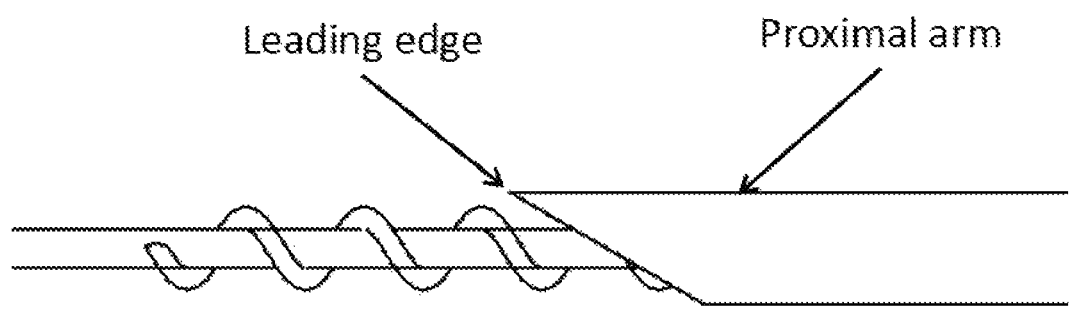
FIGS. 18A and 18B. The proximal arm of extractor with cutting edge and larger extraction path.
Figure 18B:
Figure 19A:
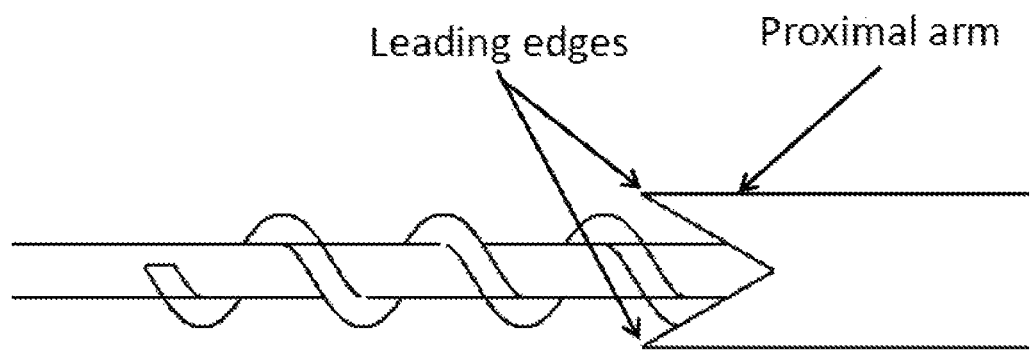
FIGS. 19A and 19B. The proximal arm of extractor may have more than one leading edge.
Figure 19B:
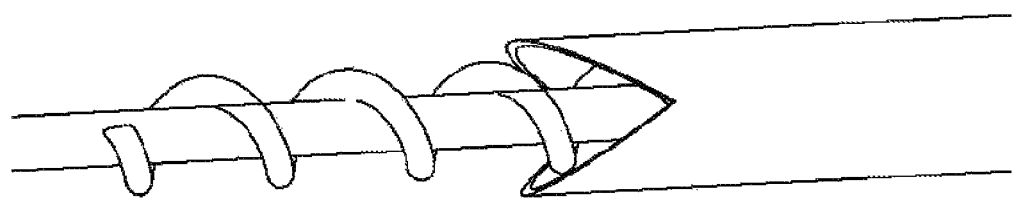
Figure 20:
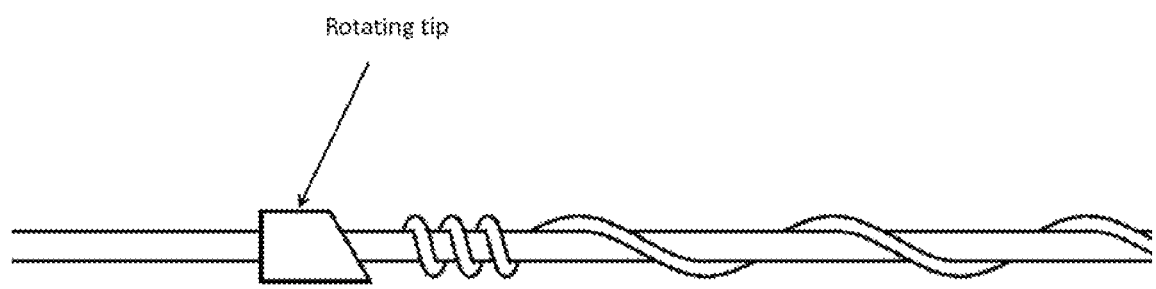
FIG. 20. Image of the macerator with a rotating tip/cutting edge. The tip rotates with the helical formation.
Figure 21:
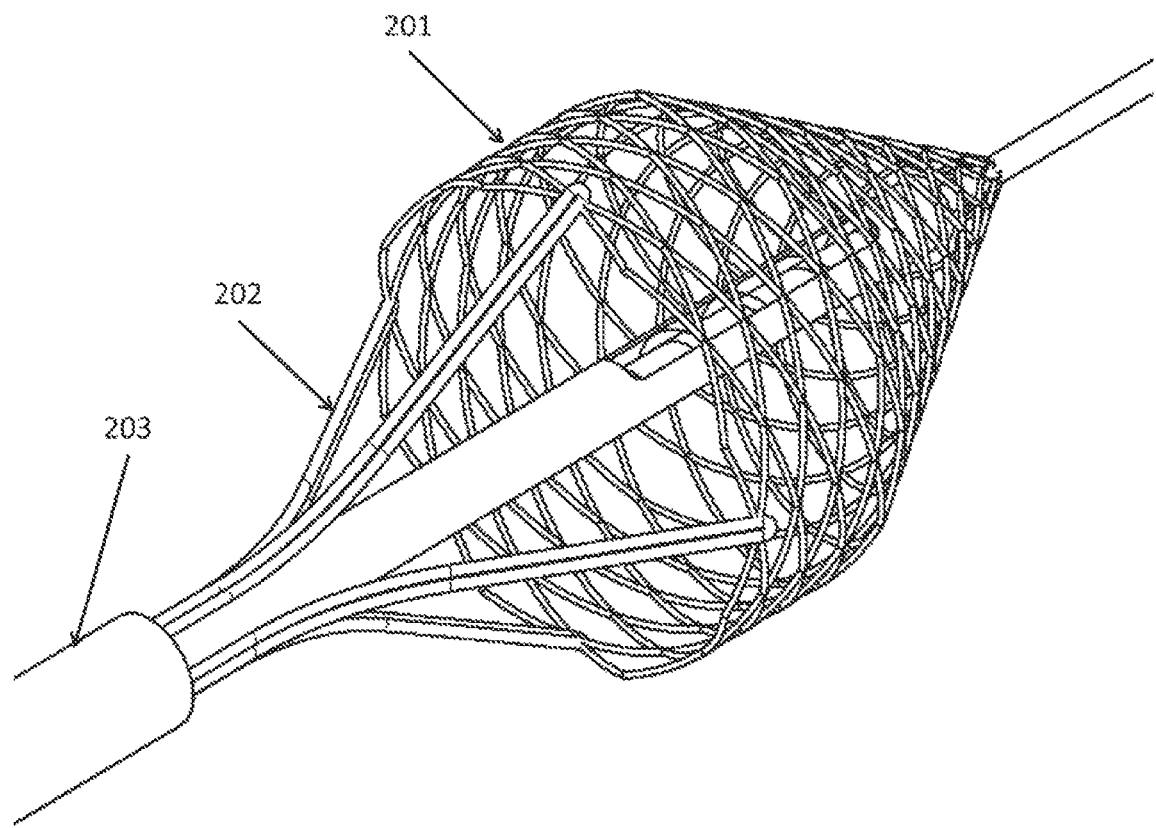
FIG. 21. Shows the cage in its open configuration. The passageway provided by the proximal arm, may be located inside the cage.
Figure 22:
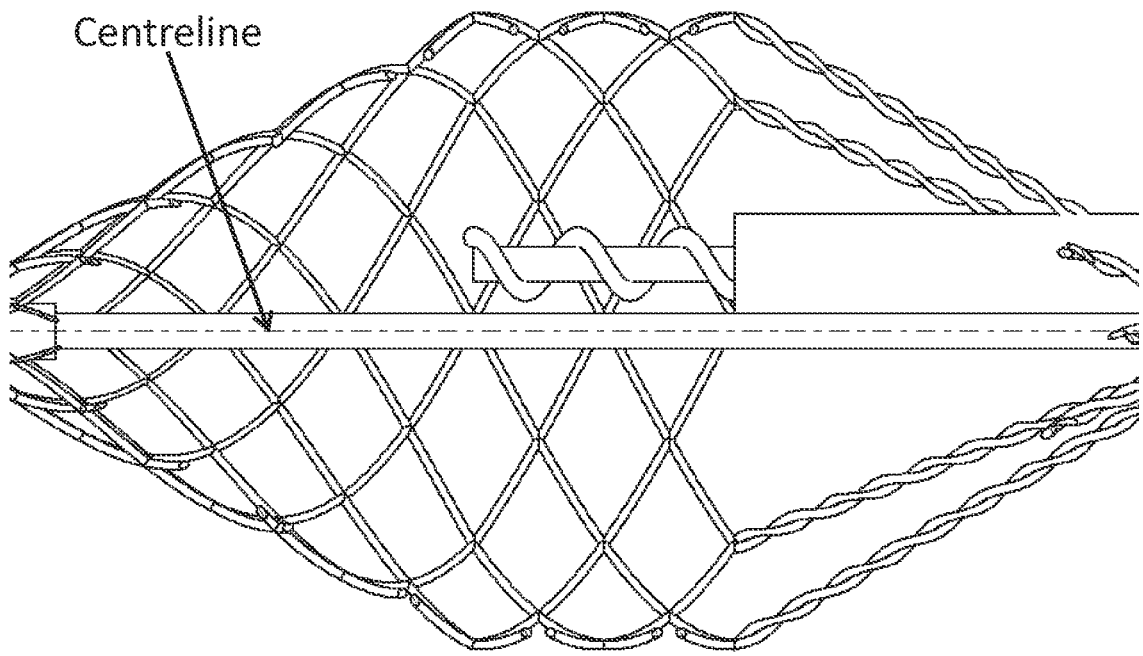
FIG. 22. The extractor may be eccentric to the centreline of the cage.
Figure 23:
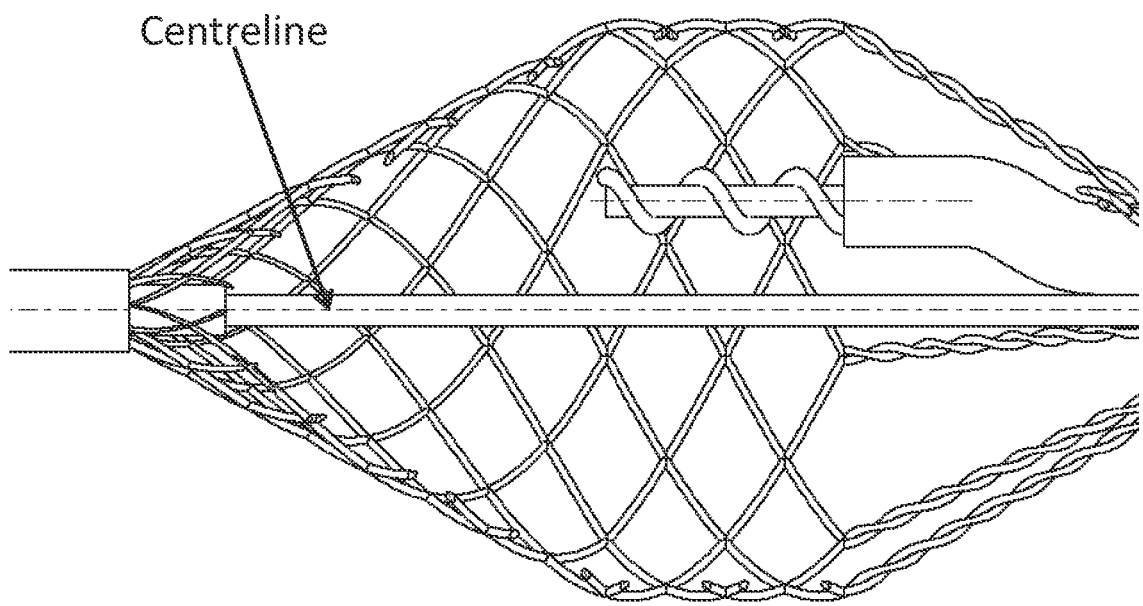
FIG. 23. The tip of the extractor may be eccentric and positioned away from the centreline of the cage.

The proximal arm may also contain a side window (FIG. 17) to improve access of the extractor to thrombus. The extractor may also be formed from one machined part rather than a wire wrapped around a tube. The rotating extractor will likely contain sharp cutting edges at its distal end to break up matter prior to extracting it. The non-rotating proximal arm may also have a leading edge/cutting element (FIGS. 18A and 18B) which helps to break down thrombus, while also increasing the size of the path at the entrance of the extractor. The proximal arm may have more than one leading edge/cutting element to break down matter; FIGS. 19A, and 19B show the proximal arm with two leading edges. The leading edge/cutting element may form part of the proximal arm (as shown) or alternatively be a separate part attached to the non-rotating proximal arm. The extractor may also contain an additional port at the proximal end where suction can be added to enhance thrombus extraction, and to attract thrombus towards the extractor. FIG. 20 shows an embodiment in which the rotating tip and helical wire are attached to the distal arm for rotation therewith. FIG. 21 shows the extractor with the cage. The extractor may also be eccentric to the centre of the cage; FIG. 22 shows the extractor eccentric to the centre cage and adjacent to it while FIG. 23 shows the tip of the cage away from the centre of the cage. In both FIGS. 22 and 23 the extractor may be stationary or rotate around the centreline.

Figure 24:
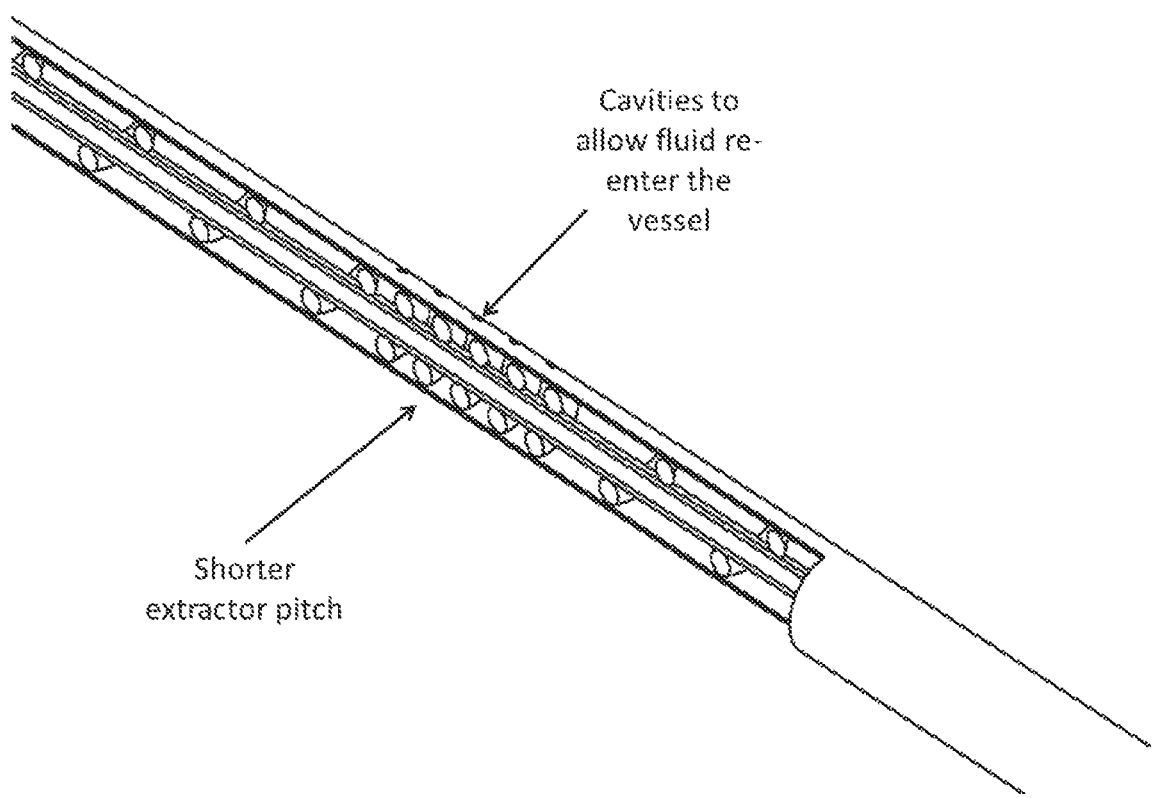
FIG. 24. Section view—the extractor may contain a region with a shorter pitch. This may compress the debris being extracted and allow fluid to flow back through the cavities and into the vessel.

The extractor may have a varied pitch along its length. One embodiment of this is shown in FIG. 24, where a section of the extractor has a reduced pitch, and the non-rotating tube has a number of small holes (acting as a filter) in it. This may allow any debris to be squeezed, forcing residual fluid through the holes and into the vessel while the remaining debris continues to be extracted.

The extraction mechanism in combination with the cage may have various functions along the device. In one embodiment, the extractor breaks down the thrombi into relatively big pieces which are small enough to enter the inlet of tube and big enough not to pass through the filter. Once the thrombus is inside the tube, the extractor, breaks them down into smaller pieces, make it easier to transfer along the catheter. Then, the extraction system may have a means of extraction such as helical wire or vacuum. The matter removed will be collected in a suitable collection means, for example a blood bag, or syringe or similar.

The helical formation may have a cutting edge, and which is adapted to rotate with the helical formation and cut or break up thrombus for extraction. The cutting edge may be a blade ore the like, and may be disposed at or close to an end of the helical formation. The extractor tube may also have a cutting edge, and may be adapted to rotate.

Combination of the Cage and Extractor

Figure 25:
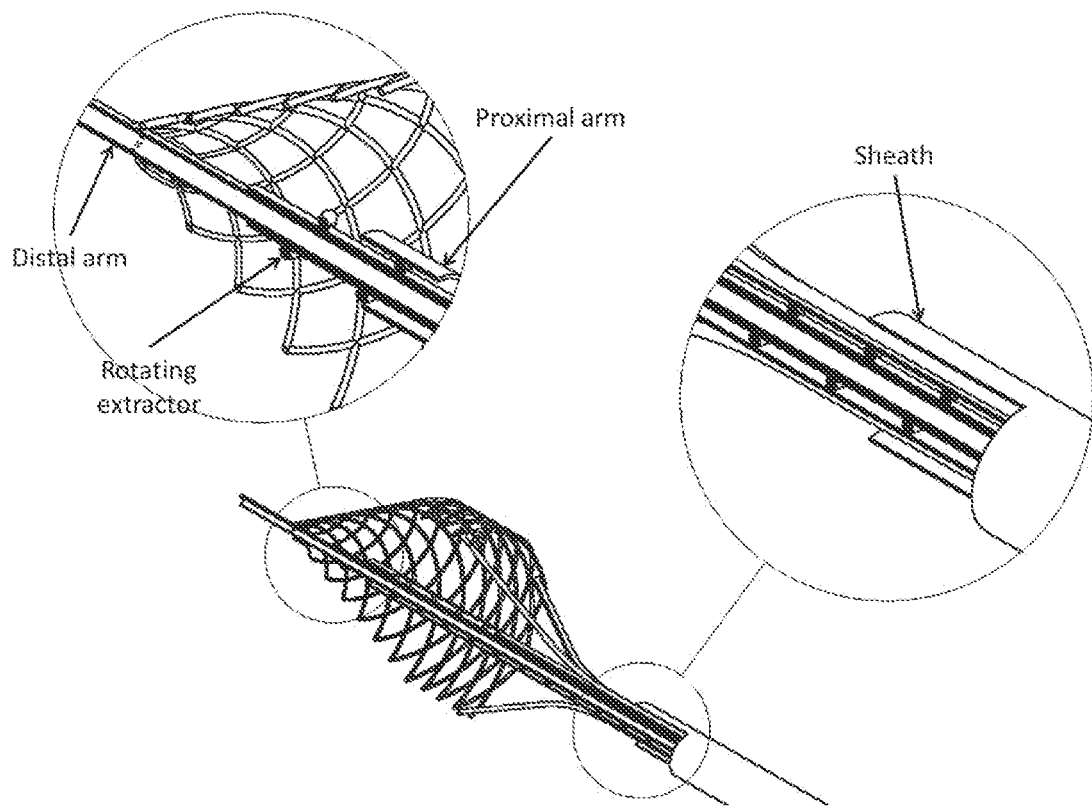
FIG. 25. Section view—Combination of the cage and the extractor. The cage is opened and closed by the relative movement of the proximal and distal arms. The rotating extractor rotates over the distal arm and within the proximal arm. A sheath can run over the device to ensure the cage is closed during delivery and retrieval.

The device contains both a cage with a self adjustment mechanism, and an extractor. FIG. 25 shows an embodiment of the distal end of the device. The device is opened and closed by the relative movement of the proximal and distal arms, while the extractor rotates over the distal arm and within the proximal arm. The proximal arm may also contain a window for extraction. A sheath covers the entire device during delivery and retrieval.

Figure 26:
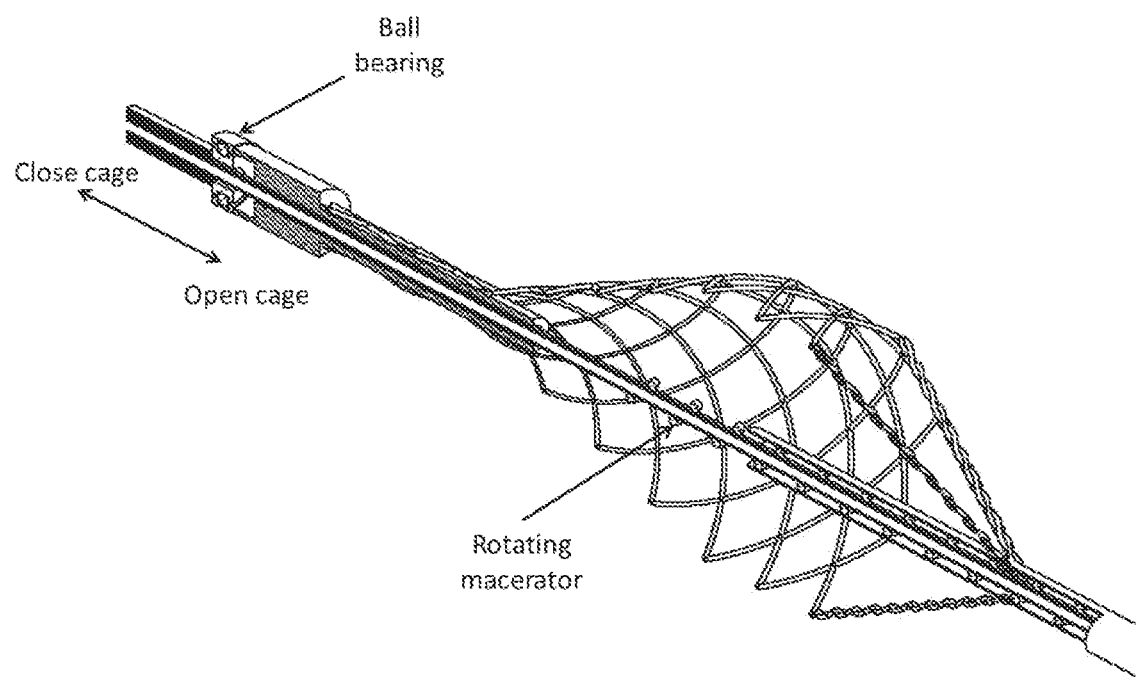
FIG. 26. Section view—The distal end of the device showing an embodiment of the cage with the extractor tube acting also as the distal arm. As the distal arm moves proximally, the cage opens. As the distal arm moves distally, the cage closes.
Figure 27:
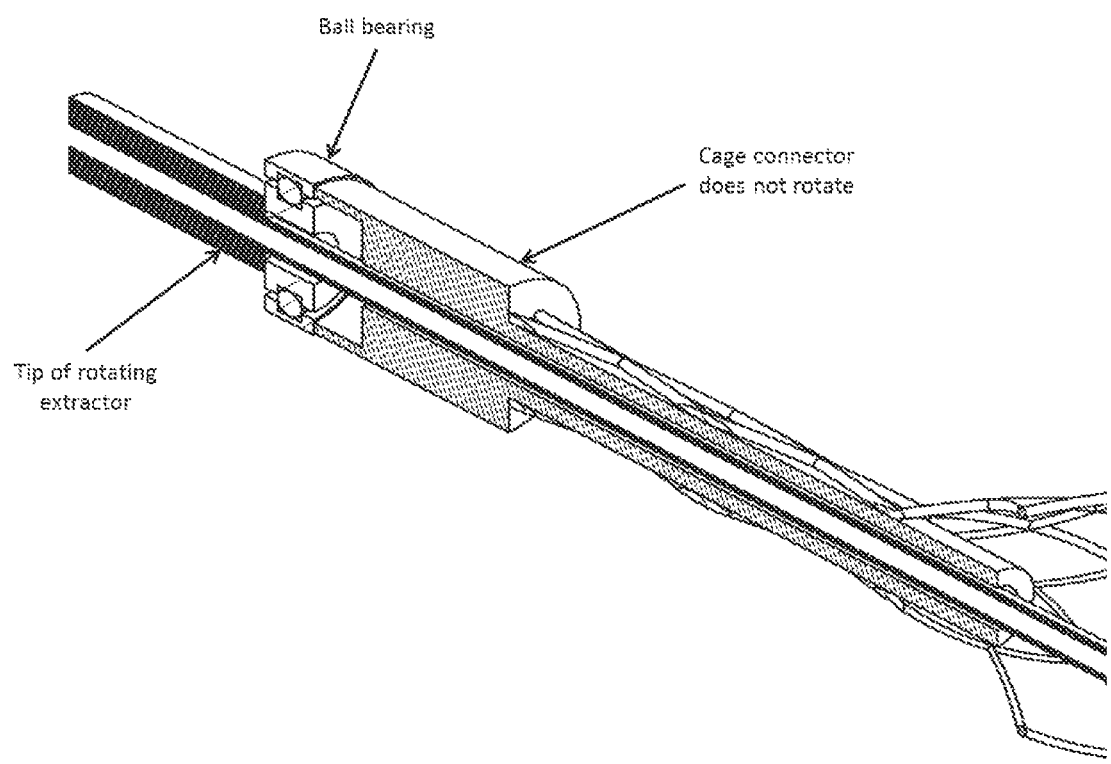
FIG. 27. Section view—The tip of the device. In this embodiment the extractor tube also acts at the distal arm. The extractor tube rotates at high speed while cage connector does not rotate. The bearing facilitates this relative movement.

FIG. 26 shows another embodiment of the distal end of the device, with the cage and extractor combined. In this embodiment, the rotating extractor also acts at the distal arm; the relative movement of which opens and closes the cage. A ball bearing has been included to facilitate contact of the rotating extractor/distal arm and non-rotating proximal arm and cage (FIG. 27).

Device With Control Mechanism Within Cage

Figure 28:
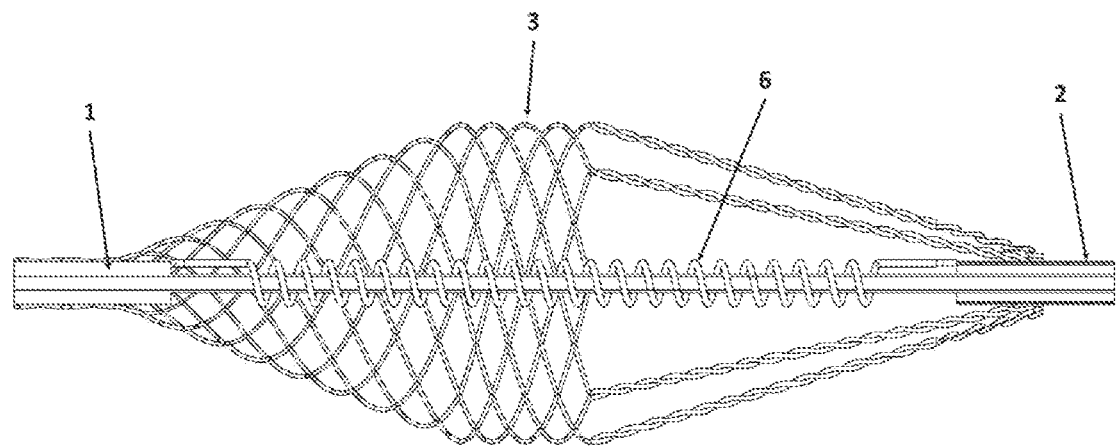
FIG. 28. Schematic of a device of the invention with a control mechanism located within the cage.

FIG. 28 shows an embodiment of the device in which the control mechanism is disposed within the cage. In this embodiment, a control mechanism is provided within the cage (3) and comprises a first part operably connected to the proximal arm (2), a second part operably connected to the distal arm (1), and a helical spring (6) connecting the first and second parts. In use, as the cage passes along a vessel that is tapering inwardly, the control mechanism ensures that a force controlled resistance is applied to the cage as it contracts, thereby ensuring that the cage remains in contact with the walls of the vessel.

Device With Control Mechanism Mounted Distally of Cage

Figure 29:
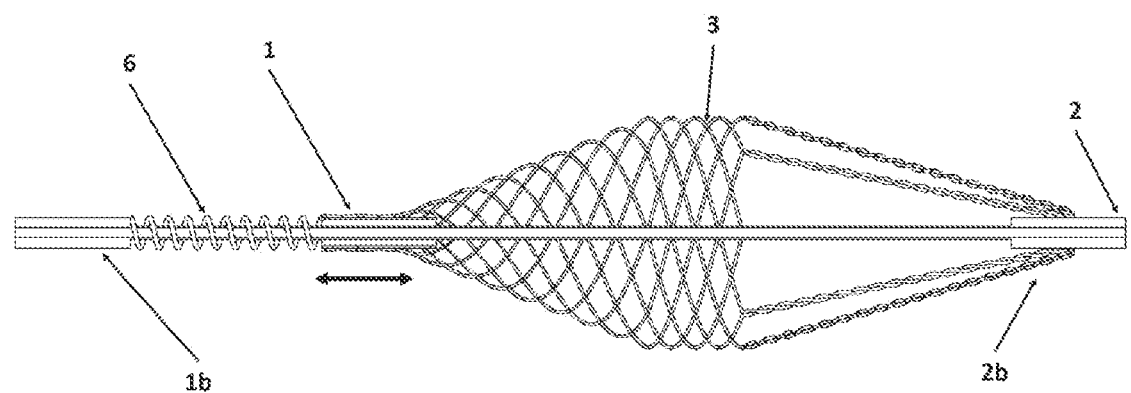
FIG. 29. Schematic of a device of the invention with a control mechanism located distally of the cage.

FIG. 29 shows an embodiment of the device in which the control mechanism is disposed distally of the cage. In this embodiment, the device comprises a proximal arm (2), which is connected to a proximal part (2b) of the cage and which extends through, and distally beyond, the cage, and a distal arm (1) which extends distally of the cage (3). The control mechanism comprises a first part (block 1b) operably connected to an end of the proximal arm, a second part operably connected to the distal arm (1), and a helical spring (6). In use, as the cage passes along a vessel that is tapering inwardly, the control mechanism ensures that a force controlled resistance is applied to the cage as it contracts, thereby ensuring that the cage remains in contact with the walls of the vessel.

Device With Outer Sheath

Figure 30:
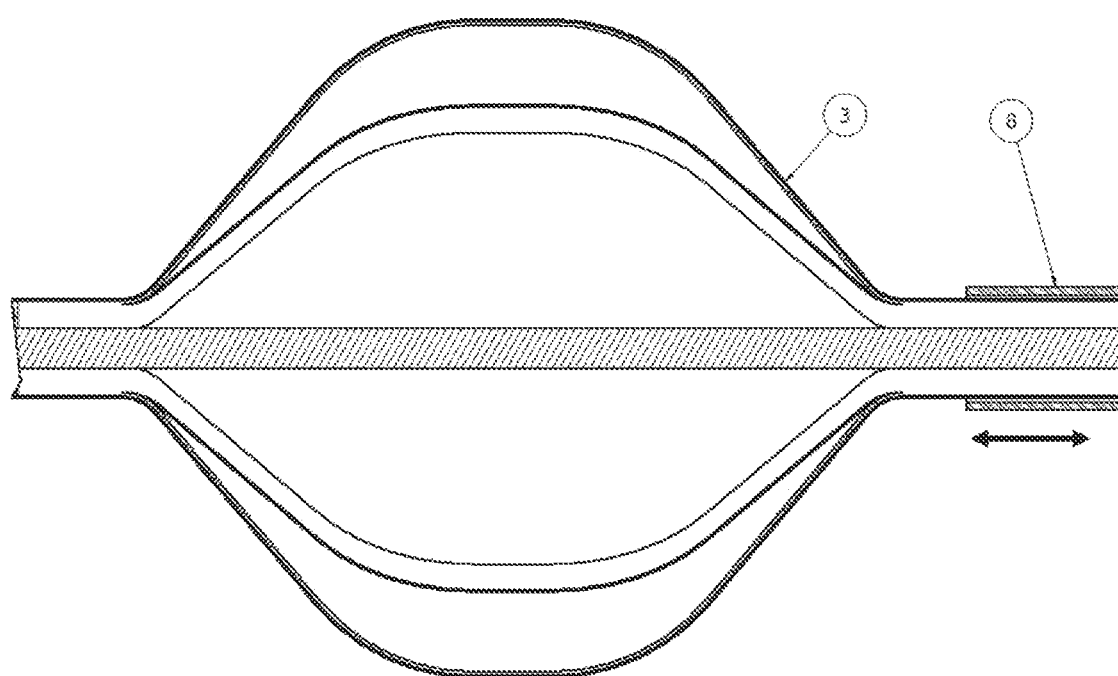
FIG. 30. Schematic of the device having a sheath covering the elongated control member and adjustable to cover the cage.
Figure 31:
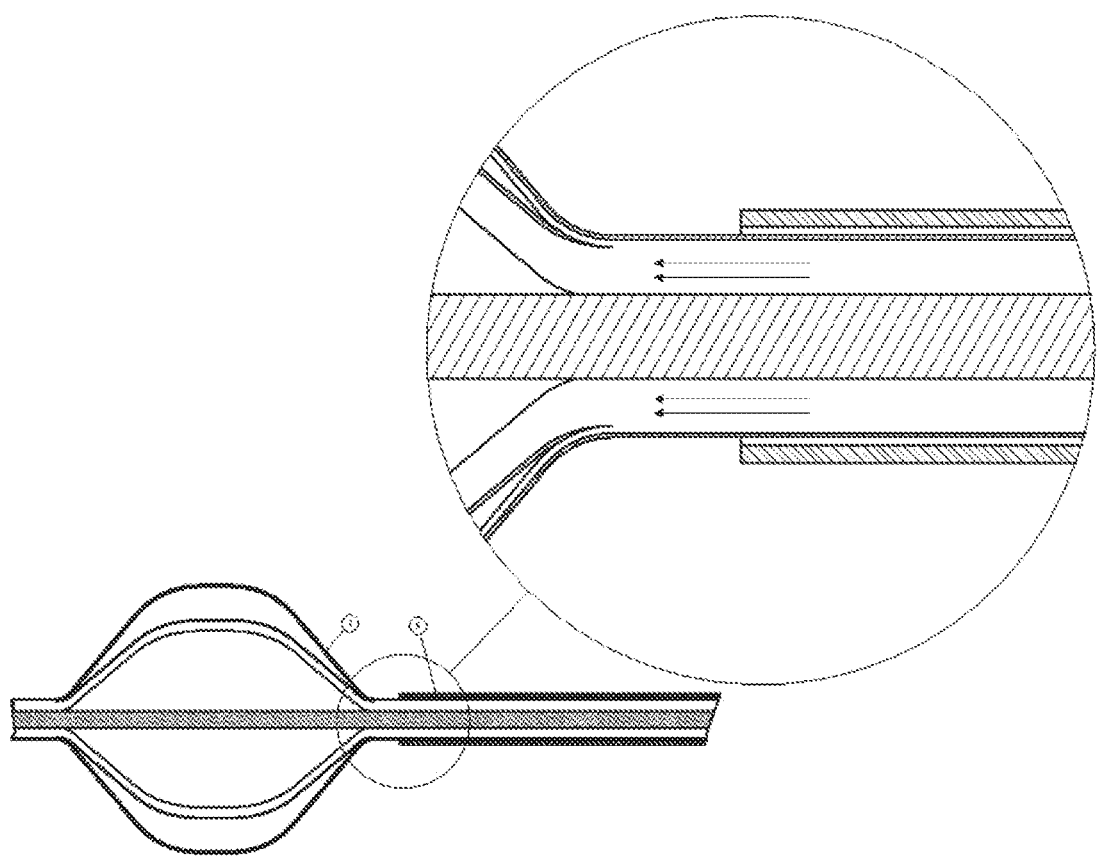
FIG. 31. Schematic of the device of the invention showing how thrombolytic agents may be infused through the extractor.
Figure 32:
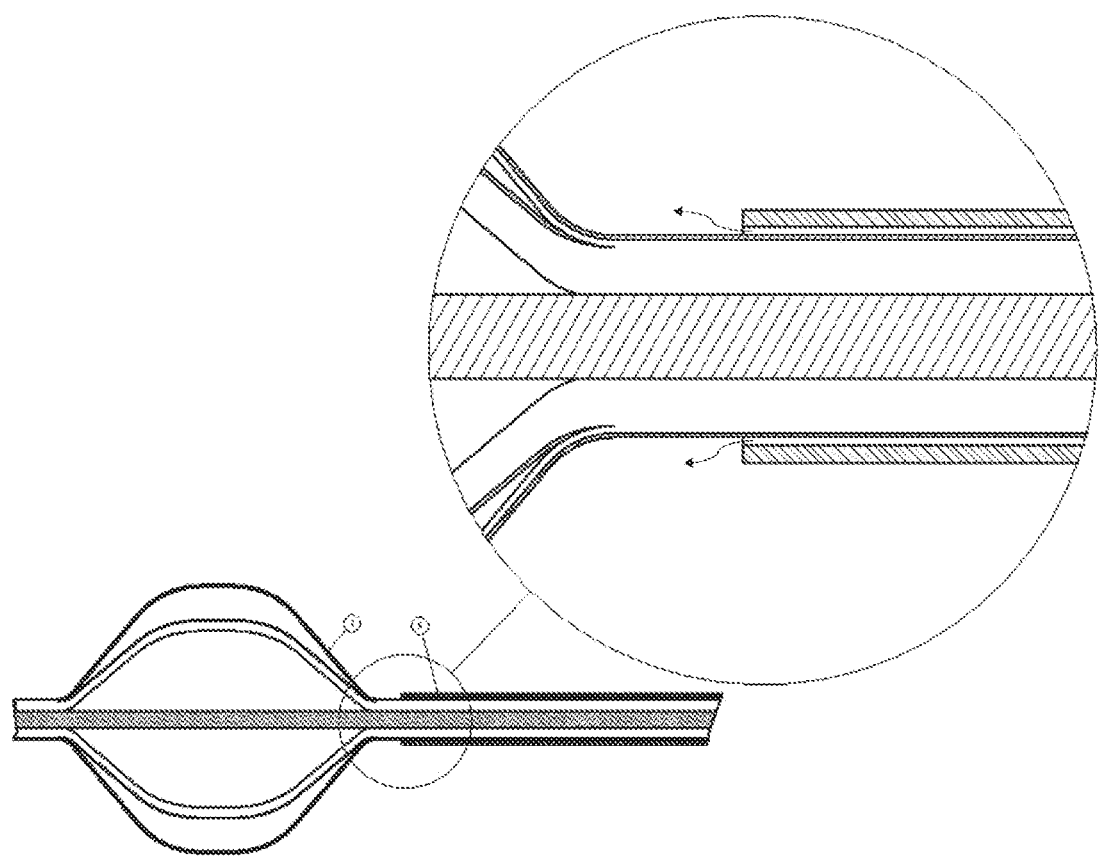
FIG. 32. Schematic of the device of the invention showing how thrombolytic agents may be infused between the extractor and the sheath FIG. 33. Schematic of the device of the invention showing how thrombolytic agents may be infused through holes or perforations formed in the sheath.
Figure 33:
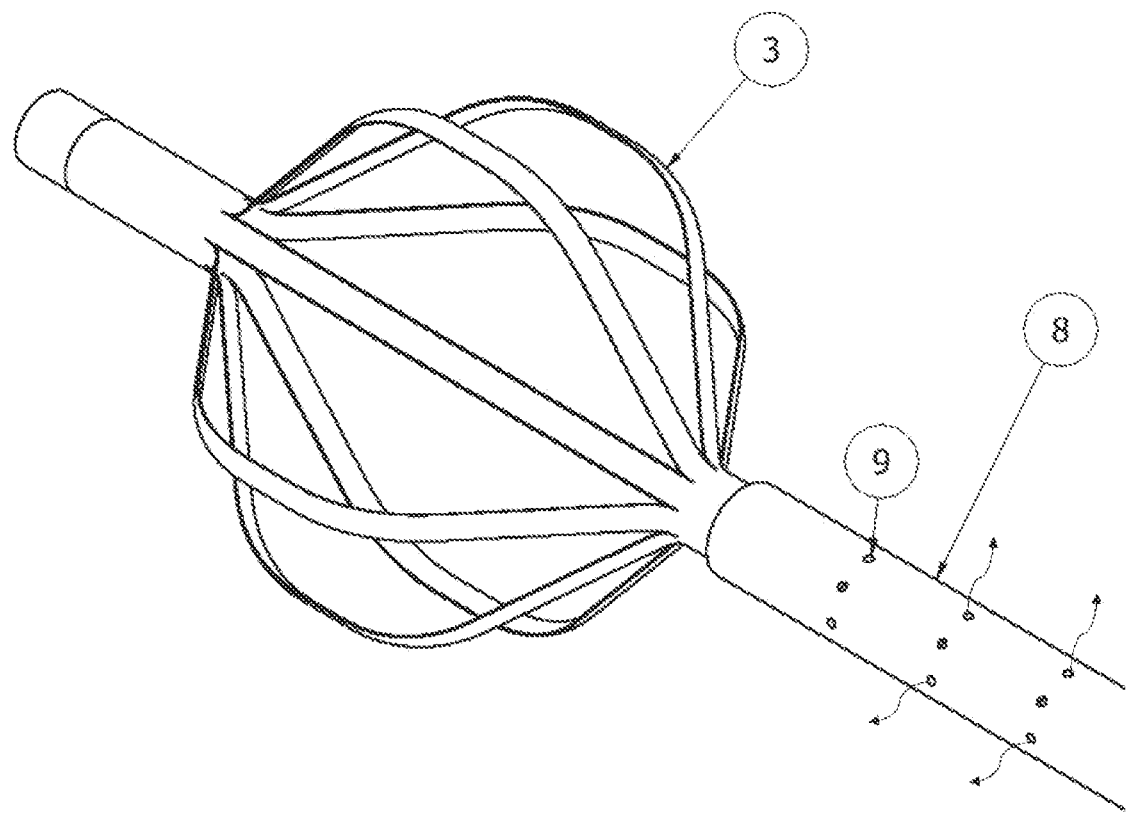
Figure 34:
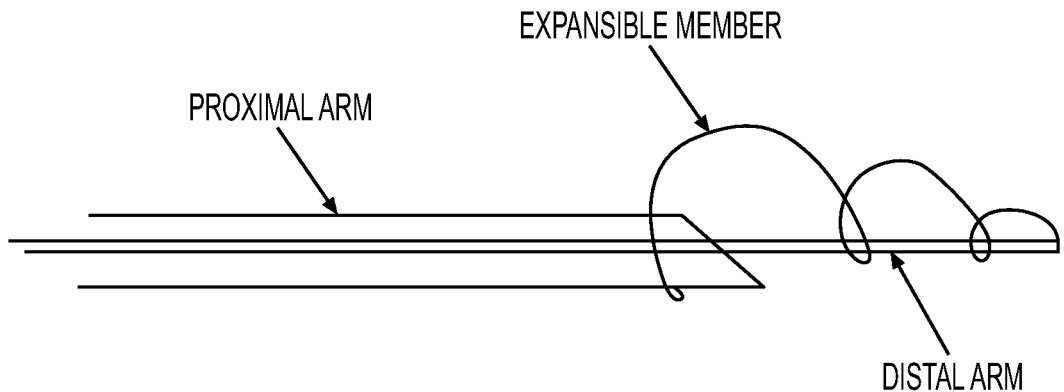
FIG. 34. Schematic of a radially expansible member formed from a single strut.
Figure 35A:
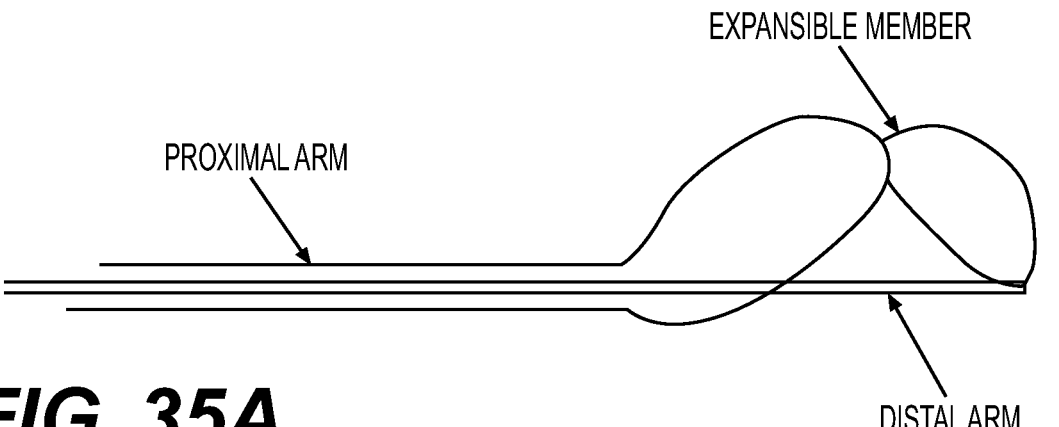
FIGS. 35A and 35B. Schematic of a radially expansible member formed from two struts.
Figure 35B:
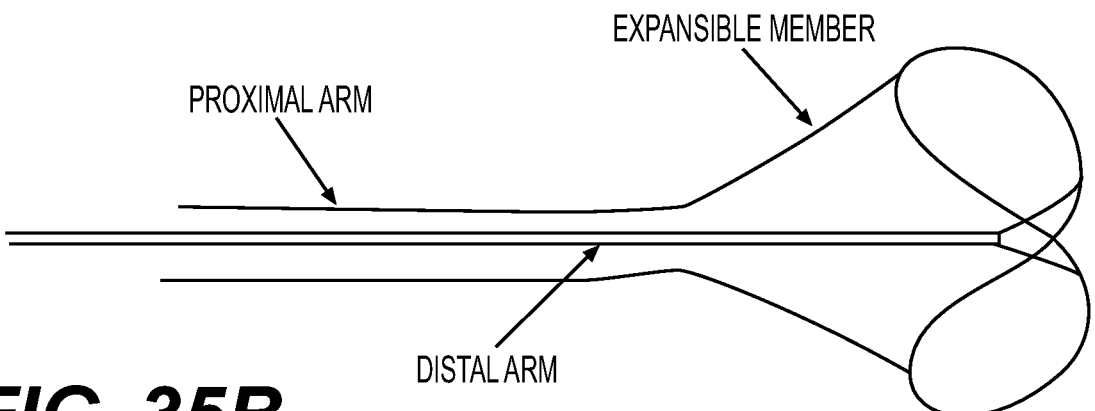
Figure 36:
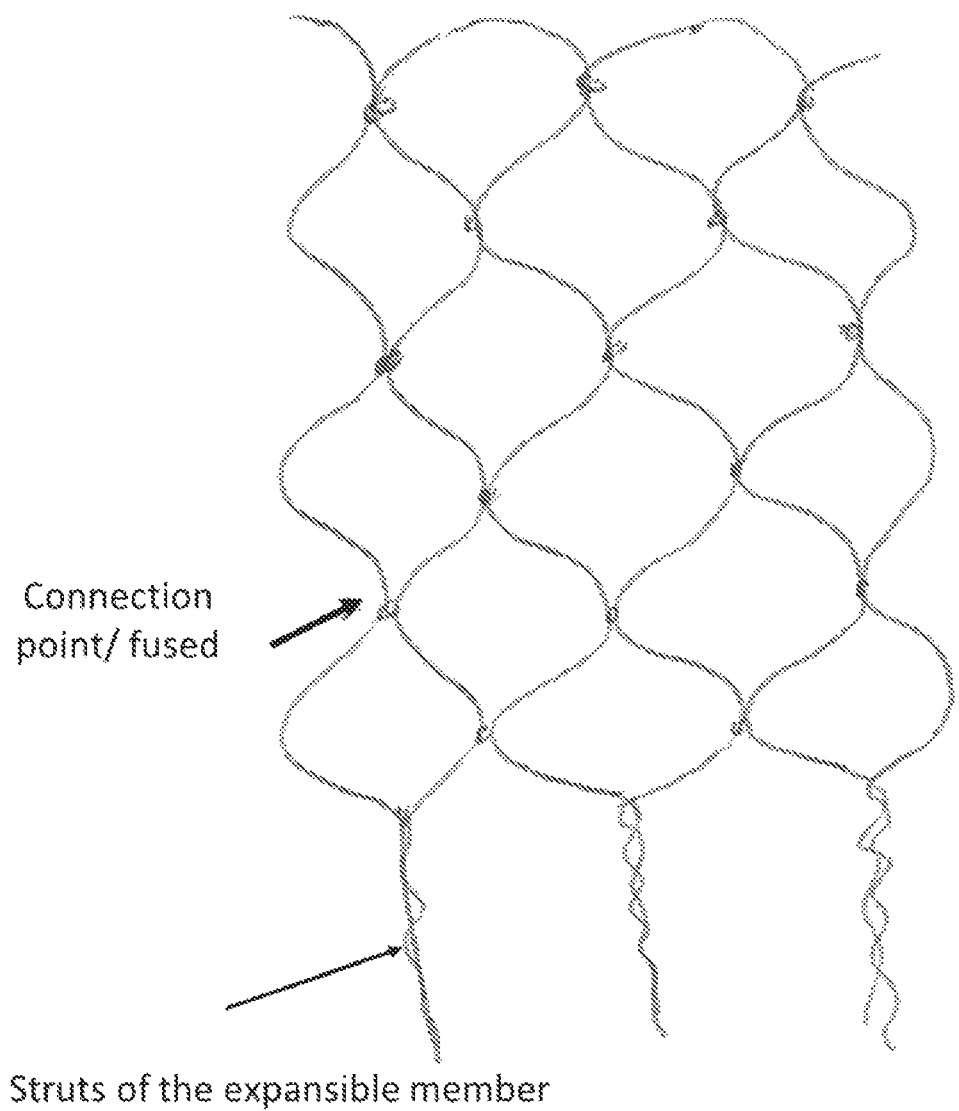
FIG. 36. An example of the radially expansible member made from a series of wires, and fused or twisted for connection (shown as a flat pattern).
Figure 37:
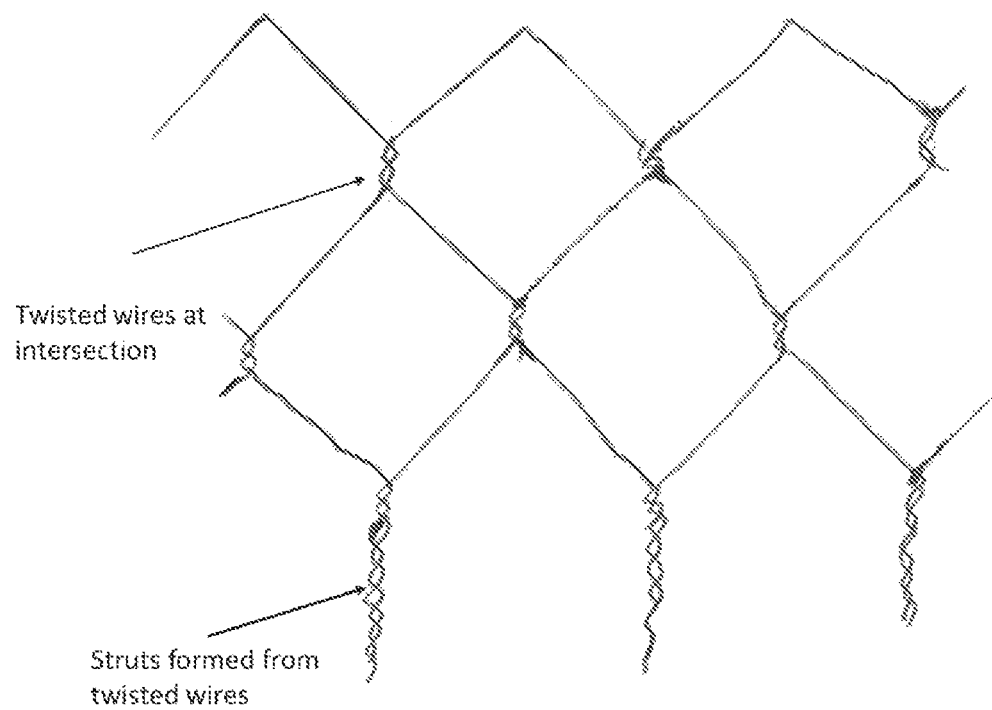
FIG. 37. An example of a braided expansible member with the wires twisted at the intersections to limit the movement of the wires with respect to each other (shown as a flat pattern).
Figure 38:
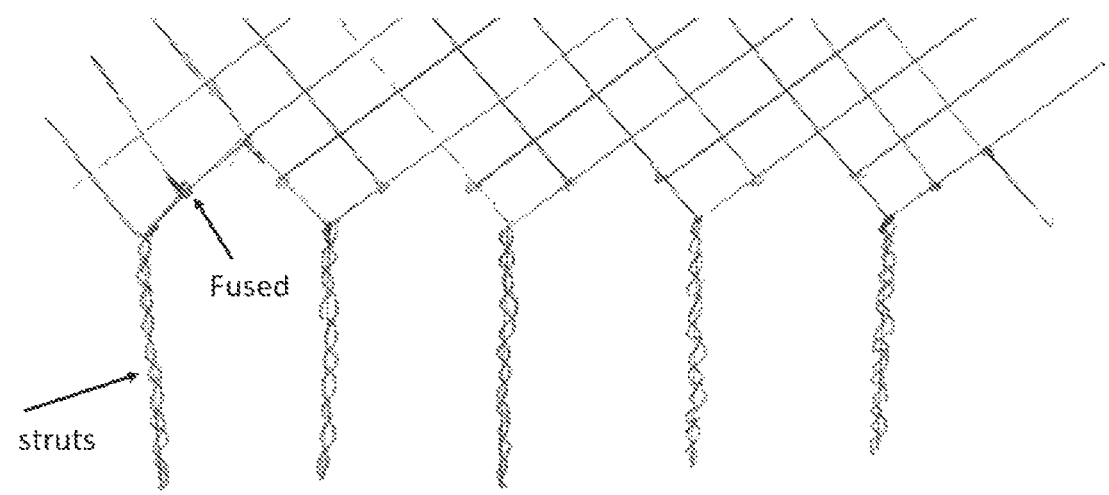
FIG. 38. An example of a braid configuration for the creation of a braided radially expansible member, with twisted wires (for struts) and fused ends (shown as a flat pattern).
Figure 39:
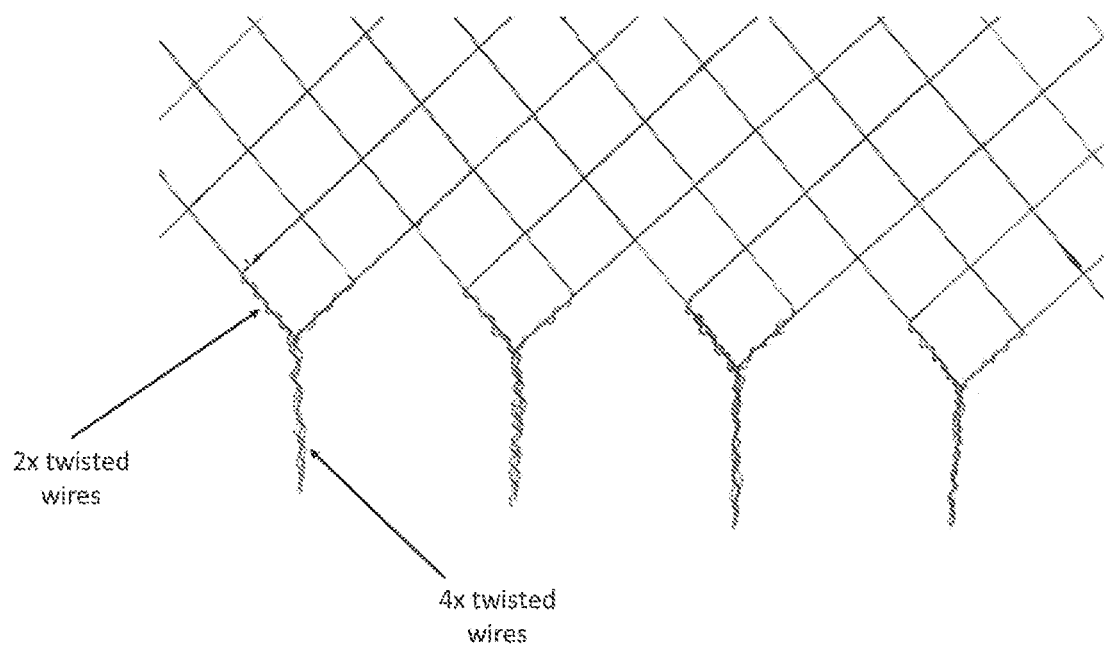
FIG. 39. An example of a braid configuration for the creation of a braided radially expansible member, with twisted wires to create struts.

Specifically, FIG. 30 shows an embodiment of the device of the invention in which a sheath (8) is provided that covers the elongated control member. In this embodiment, the device can be manipulated such that the cage (3) is contracted and withdrawn within the sheath, which will thus keep it in a contracted orientation Delivery of Liquid Agent to Vessel Lumen The device of the invention may also be employed to deliver liquid agent, for example a thrombolytic agent which can break down thrombus, to the vessel lumen. This may be achieved in a number of different ways including:

The direction of rotation of the extractor screw can be changed to infuse rather than extract.
    Inject through the hollow distal arm.
    Inject through a lumen between the distal arm and the extractor tube (proximal arm) (FIG. 31)
    Injected in between the extractor tube (proximal arm) and the sheath (FIG. 32).
    Injected through cavities in the sheath (FIG. 33).
    The location of the sheath and cavities can be adjusted along the catheter length.
    One of, or a combination of, the above methods of infusion.

Generally, the liquid agent would be injected into the delivery lumen, which may be any of the above. Alternatively, the liquid agent may be delivered slowly by means of a drip feed. AS indicated above, the liquid agent may be delivered in a number of different ways, for example through a hollow distal arm (which has the advantage of being capable of delivering liquid agent distally of the cage), through a lumen formed between the distal arm and the proximal arm (also referred to as the extractor tube), or through a lumen formed between the proximal arm and the outer sheath.

Design of Radially Expansible Member

FIGS. 34 to 39 describe embodiments of the radially expansible member forming part of the device of the invention, and specifically braid configurations that may be employed in radially expansible members.

The invention is not limited to the embodiments hereinbefore described which may be varied in construction and detail without departing from the spirit of the invention.

The invention claimed is:

1. A thrombectomy device, comprising:
a handle at a proximal end portion of the device;
a first tube;
a second tube extending to a distal end portion of the device;
a cage at the distal end portion of the device, the cage being adjustable between a contracted orientation and an expanded orientation, the cage including a scraping element formed with one or more of a round wire, a flat wire, or a blade disposed between a proximal end portion of the cage and a distal end portion of the cage, the scraping element being configured to remove matter from a body lumen when the cage is in the expanded orientation;
a suction device including an opening formed in a side wall of the second tube, including a source of suction connected to the proximal end portion of the device, the suction device being configured to apply suction towards an interior of the second tube and to an extraction passage formed between the first tube and the second tube in a radial direction;
wherein the opening extends between the scraping element and a distal end of the device in a proximal to distal direction; and
wherein the scraping element is positioned at a widest portion of the cage.

2. The device of claim 1, wherein the opening has an approximately rectangular shape.

3. The device of claim 1, further including a mechanical extractor extending within the extraction passage.

4. The device of claim 3, wherein the suction device is configured to apply suction to an interior of the second tube.

5. A thrombectomy device, comprising:
a proximal end portion;
a distal end portion;
a radially-expandable cage at the distal end portion, the cage including struts forming a plurality of proximal openings and a plurality of distal openings, at least one of the proximal openings being larger than one or more of the distal openings;
a scraping element disposed at the cage, the scraping element being configured to remove matter from a body lumen by applying a shearing force;
a vacuum device in fluid communication with an interior of the radially-expandable cage via a window formed radially inwardly of one or more of the distal openings; and
wherein the window extends distally of the proximal openings.

6. The device of claim 5, further comprising an extractor, the extractor having a helical portion extending within the window.

7. The device of claim 5, wherein the struts include a wire that defines a portion of one or more of the distal openings and a portion of one or more of the proximal openings.

8. The device of claim 5, wherein the distal openings are formed in a portion of the cage that gradually narrows toward the distal end portion of the device.

9. The device of claim 5, wherein the window is formed within a distal tube that extends from a handle of the device to the distal end portion of the device.

10. The device of claim 5, wherein the vacuum device is in fluid communication with a plurality of openings formed in a tube extending from a handle of the device to the distal end portion of the device.

11. A thrombectomy device, comprising:
a first tube connected to a handle at a proximal end portion of the device;
a second tube extending to a distal end portion of the device;
a cage at the distal end portion of the device, the cage being adjustable between a contracted orientation and an expanded orientation by an axial motion of the first tube or the second tube, the cage including:
    a scraping element disposed between a proximal end portion of the cage and a distal end of the cage;
    proximal openings and distal openings, at least one side of each proximal opening being defined by plural wires;
    wherein the plural wires are twisted together forming twisted wires;
    wherein the twisted wires include first portions that define the proximal openings and second portions that define one or more distal openings, the second portions being less tightly twisted as compared to the first portions, and the scraping element is formed at an intersection of the first and second portions;

a passageway extending from the cage to the proximal end portion of the device, the passageway being sized to receive material removed from a body lumen by the scraping element; and a vacuum in fluid communication with the passageway and with an opening formed in the second tube, the vacuum being configured to draw the material removed from the body lumen towards the passageway via the opening.

12. The device of claim 11, wherein the passageway is formed within the second tube.

13. The device of claim 12, further including a rotatable helical structure within the passageway.

* * * * *